United States Patent [19]

Kirchhoff et al.

[11] Patent Number: 5,876,734
[45] Date of Patent: Mar. 2, 1999

[54] POLYPEPTIDES FOR DIAGNOSING INFECTION WITH *TRYPANOSOMA CRUZI*

[76] Inventors: Louis V. Kirchhoff, 204 Lexington Ave., Iowa City, Iowa 52246-2413; Keiko Otsu, 601 Normandy Dr., Iowa City, Iowa 52246-2928

[21] Appl. No.: 216,894

[22] Filed: Mar. 24, 1994

[51] Int. Cl.[6] .................................................. A61K 39/002
[52] U.S. Cl. ................................. 424/269.1; 424/192.1; 424/193.1; 530/300; 530/350; 435/7.22
[58] Field of Search ................................... 530/300, 350; 424/192.1, 269.1, 193.1; 435/7.22

[56] References Cited

U.S. PATENT DOCUMENTS

| 4,801,530 | 1/1989 | Nogueira et al. | 435/6 |
| 4,870,006 | 9/1989 | Dragon et al. | 435/7 |
| 5,482,708 | 1/1996 | Spibey et al. | 424/187.1 |

FOREIGN PATENT DOCUMENTS

| WO 91/15584 | 10/1991 | WIPO . |
| WO 92/09895 | 6/1992 | WIPO . |
| WO 93/16199 | 8/1993 | WIPO . |
| WO 94/01776 | 1/1994 | WIPO . |

OTHER PUBLICATIONS

Lorca et al. "Immunodetection of Antibodies In Sera From Symptomatic And Asymptomatic Chilean Chagas' Disease Patients With *Trypanosoma Cruzi* Recombinent Antigens," *Am. J. Trop. Med. Hyg.* 46: 44–49 (1992).

Krieger et al, "Use of Recombinant Antigens For The Accurate Immunodiagnosis Of Chagas' Disease," Am. J. Trop. Med. Hyg. Am. J. Trop. Med. Hyg.46: 427–434 (1992).

Lovca et al. "Diagnosis Of Chronic Chagas Disease Using ReCombinant *Trypanosoma cruzi* Antigens," *Rev. Med. Chile* 121:363–358 (1993).

Pastini et al. "Immunoassay With Recombinant *Trypanosoma cruzi* Antigens Potentially Useful For Screening Donated Blook And Diagnosing Chagas Diseases," *Clin. Chem.* 40:1893–1897 (1994).

Bastos et al. "Evaluaiton Of Recombinant *T. cruzi* Antigens In The Serological Diagnosis Of Chagas Disease. Comparison With Conventional Serology, PCR and Xenodiagnosis," *Mem. Inst. Oswalde Cruz* 90 (Suppl):33 (1995).

Krettli et al, "Use Of *Trypanosoma cruzi* Purified Antigens And Recombinant Proteins in Elisa To Monitor Cure of Human Chagas' Disease," *Mem. Inst. Oswalde Cruz* 90(Suppl):30–31 (1995).

Camargo, "American Trypanosomiasis (Chagas' Disease)." *Laboratory Dianosis of Infectious Diseases—Principles and Practice*, vol. I, Chap. 77, pp. 744–753.

Kirchhoff et al., "Cryptic Epitope Explains the Failure of a Monoclonal Antibody to Bind to Certain Isolates of *Trypanosoma Cruzi*." *The Journal of Immunology*, vol. 133, No. 5, pp. 2731–2735 (Nov. 1984).

Ibanez et al., "Multiple *Trypanosoma Cruzi* Antigens Containing Tandemly Repeated Amino Acid Sequence Motifs." *Molecular and Biochemical Parasitology*, vol. 30, pp. 27–34 (1988).

Smith et al., "Single–Step Purification of Polypeptides Expressed in *Escherichia Coli* as Fusions with Glutathione S–Transferase." *Gene*, vol. 67, pp. 31–40 (1988).

Engman et al., "Comparison of HSP70 Genes from Two Strains of *Trypanosoma Cruzi*." *Molecular and Biochemical Parasitology*, vol. 37, pp. 285–288 (1989).

Hoft et al., "*Trypanosoma Cruzi* Expresses Diverse Repetitive Protein Antigens." *Infection and Immunity*, vol. 57, No. 7, pp. 1959–1967 (Jul. 1989).

Lafaille et al., "Structure and Expression of Two *Trypanosoma Cruzi* Genes Encoding Antigenic Proteins Bearing Pepetitive Epitopes." *Molecular and Biochemical Parasitology*, vol. 35, pp. 127–136 (1989).

Cotrim, et al., "Expression in *Escherichia Coli* of a Dominant Immunogen of *Trypanosoma Cruzi* Recognized by Human Chagasic Sera." *Journal of Clinical Microbiology*, vol. 28, No. 3, 519–524 (Mar. 1990).

Moncayo et al., "Multicentre Double Blind Study for Evaluation of *Trypanosoma Cruzi* Defined Antigens as Diagnostic Reagents (+)." *Mem. Inst. Oswaldo Cruz, Rio de Janeiro*, vol. 85 (4), pp. 489–495 (1990).

Frasch et al., "Comparison of Genes Encoding *Trypanosoma Cruzi* Antigens." *Parasitology Today*, vol. 7, No. 6, pp. 148–151 (1991).

Levin et al., "Recombinant *Trypanosoma Cruzi* Antigens and Chagas' Disease Diagnosis: analysis of a workshop." *FEMS Microbiology Immunology*, vol. 89, pp. 11–20 (1991).

Burns et al., "Identification and Synthesis of a Major Conserved Antigenic Epitope of *Trypanosoma Cruzi*." *Proc. Natl. Acad. Sci. USA*, vol. 89, pp. 1239–1243 (Feb. 1992).

Otsu et al., "Interruption of a *Trypanosoma Cruzi* Gene Encoding a Protein Containing 14–Amino Acid Repeats." *Molecular and Biochemical Parasitology*, vol. 57, pp. 317–330 (1993).

*Primary Examiner*—James C. Housel
*Assistant Examiner*—Jennifer E. Shaver
*Attorney, Agent, or Firm*—Foley & Lardner

[57] ABSTRACT

Polypeptides are disclosed that are useful for diagnosing American trypanosomiasis, or Chagas disease, a disease caused by the infectious agent *Trypanosoma cruzi*. The polypeptides have a sequence that corresponds to the amino acid sequence of at least one of the C-terminal and N-terminal nonrepetitive regions of TCR27 protein. The polypeptide additionally may comprise an amino acid sequence of one or more repeats from the central region of TCR27 protein. In a preferred embodiment, the polypeptide corresponds to the N-terminal nonrepetitive region of TCR27 protein and at least one repeat from the central region of TCR27 protein, and does not correspond to the C-terminal nonrepetitive region. The polypeptides may further comprise a linker sequence at either the N-terminus or the C-terminus to facilitate attachment or conjugation to a carrier molecule in a liquid or solid support system for use in a sensitive assay for detecting *T. cruzi* infection.

6 Claims, 19 Drawing Sheets

FIG. 2A-1

```
  M   S   P   I   L   G   Y   W   K   I   K   G   L   V   Q   P   T   R   L   L
ATGTCCCCTATACTAGGTTATTGGAAAATTAAGGGCCTTGTGCAACCCACTCGACTTCTT
---------+---------+---------+---------+---------+---------+-------60

L   E   Y   L   E   E   K   Y   E   E   H   L   Y   E   R   D   E   G   D   K
TTGGAATATCTTGAAGAAAAATATGAAGAGCATTTGTATGAGCGCGATGAAGGTGATAAA
---------+---------+---------+---------+---------+---------+-------120

W   R   N   K   K   F   E   L   G   L   E   F   P   N   L   P   Y   Y   I   D
TGGCGAAACAAAAAGTTTGAATTGGGTTTGGAGTTTCCCAATCTTCCTTATTATATTGAT
---------+---------+---------+---------+---------+---------+-------180

G   D   V   K   L   T   Q   S   M   A   I   I   R   Y   I   A   D   K   H   N
GGTGATGTTAAATTAACACAGTCTATGGCCATCATACGTTATATAGCTGACAAGCACAAC
---------+---------+---------+---------+---------+---------+-------240

M   L   G   G   C   P   K   E   R   A   E   I   S   M   L   E   G   A   V   L
ATGTTGGGTGGTTGTCCAAAAGAGCGTGCAGAGATTTCAATGCTTGAAGGAGCGGTTTTG
---------+---------+---------+---------+---------+---------+-------300

D   I   R   Y   G   V   S   R   I   A   Y   S   K   D   F   E   T   L   K   V
GATATTAGATACGGTGTTTCGAGAATTGCATATAGTAAAGACTTTGAAACTCTCAAAGTT
---------+---------+---------+---------+---------+---------+-------360

D   F   L   S   K   L   P   E   M   L   K   M   F   E   D   R   L   C   H   K
GATTTTCTTAGCAAGCTACCTGAAATGCTGAAAATGTTCGAAGATCGTTTATGTCATAAA
---------+---------+---------+---------+---------+---------+-------420

T   Y   L   N   G   D   H   V   T   H   P   D   F   M   L   Y   D   A   L   D
ACATATTTAAATGGTGATCATGTAACCCATCCTGACTTCATGTTGTATGACGCTCTTGAT
---------+---------+---------+---------+---------+---------+-------480

V   V   L   Y   M   D   P   M   C   L   D   A   F   P   K   L   V   C   F   K
GTTGTTTTATACATGGACCCAATGTGCCTGGATGCGTTCCCAAAATTAGTTTGTTTTAAA
---------+---------+---------+---------+---------+---------+-------540

K   R   I   E   A   I   P   Q   I   D   K   Y   L   K   S   S   K   Y   I   A
AAACGTATTGAAGCTATCCCACAAATTGATAAGTACTTGAAATCCAGCAAGTATATAGCA
---------+---------+---------+---------+---------+---------+-------600

W   P   L   Q   G   W   Q   A   T   F   G   G   G   D   H   P   P   K   S   D
TGGCCTTTGCAGGGCTGGCAAGCCACGTTTGGTGGTGGCGACCATCCTCCAAAATCGGAT
---------+---------+---------+---------+---------+---------+-------660

L   V   P   R   G   S   P   S   Q   L   Q   Q   A   E   N   N   I   T   N   S
CTGGTTCCGCGTGGATCCCCGTCCCAGCTCCAACAGGCAGAAAATAATATCACTAATTCC
---------+---------+---------+---------+---------+---------+-------720
```

FIG. 2A-2

```
           K  K  E  M  T  K  L  R  E  K  V  K  K  A  E  K  E  K  L  D
        AAAAAAGAAATGACAAAGCTACGAGAAAAAGTGAAAAAGGCCGAGAAAGAAAAATTGGAC
        ---------+---------+---------+---------+---------+-------780

A  I  N  R  A  T  K  L  E  E  E  R  N  Q  A  Y  K  A  A  H
        GCCATTAACCGGGCAACCAAGCTGGAAGAGGAACGAAACCAAGCGTACAAAGCAGCACAC
        ---------+---------+---------+---------+---------+-------840

K  A  E  E  E  K  A  K  T  F  Q  R  L  I  T  F  E  S  E  N
        AAGGCAGAGGAGGAAAAGGCTAAAACATTTCAACGCCTTATAACATTTGAGTCGGAAAAT
        ---------+---------+---------+---------+---------+-------900

I  N  L  K  K  R  P  N  D  A  V  S  N  R  D  K  K  K  N  S
        ATTAACTTAAAGAAAAGGCCAAATGACGCAGTTTCAAATCGGGATAAGAAAAAAAATTCT
        ---------+---------+---------+---------+---------+-------960

E  T  A  K  T  D  E  V  E  K  Q  R  A  A  E  A  A  K  A  V
        GAAACCGCAAAAACTGACGAAGTAGAGAAACAGAGGGCGGCTGAGGCTGCCAAGGCCGTG
        ---------+---------+---------+---------+---------+------1020

E  T  E  K  Q  R  A  A  E  A  T  K  V  A  E  A  E  K  R  K
        GAGACGGAGAAGCAGAGGGCAGCTGAGGCCACGAAGGTTGCCGAAGCGGAGAAGCGGAAG
        ---------+---------+---------+---------+---------+------1080

A  A  E  A  A  K  A  V  E  T  E  K  Q  R  A  A  E  A  T  K
        GCAGCTGAGGCCGCCAAGGCCGTGGAGACGGAGAAGCAGAGGGCAGCTGAAGCCACGAAG
        ---------+---------+---------+---------+---------+------1140

V  A  E  A  E  K  Q  K  A  A  E  A  A  K  A  V  E  T  E  K
        GTTGCCGAAGCGGAGAAGCAGAAGGCAGCTGAGGCCGCCAAGGCCGTGGAGACGGAGAAG
        ---------+---------+---------+---------+---------+------1200

Q  R  A  A  E  A  T  K  V  A  E  A  E  K  Q  R  A  A  E  A
        CAGAGGGCAGCTGAAGCCACGAAGGTTGCCGAAGCGGAGAAGCAGAGGGCAGCTGAAGCC
        ---------+---------+---------+---------+---------+------1260

M  K  V  A  E  A  E  K  Q  K  A  A  E  A  T  K  V  A  E  A
        ATGAAGGTTGCCGAAGCGGAGAAGCAGAAGGCAGCTGAGGCCACGAAGGTTGCCGAAGCG
        ---------+---------+---------+---------+---------+------1320

E  K  Q  K  A  A  E  A  T  K  V  A  E  A  E  K  Q  K  A  A
        GAGAAGCAGAAGGCAGCTGAAGCCACGAAGGTTGCCGAAGCGGAGAAGCAGAAGGCAGCT
        ---------+---------+---------+---------+---------+------1380

E  A  T  K  V  A  E  A  E  K  Q  K  A  A  E  A  T  K  V  A
        GAAGCCACGAAGGTTGCCGAAGCGGAGAAGCAGAAGGCAGCTGAAGCCACGAAGGTTGCC
        ---------+---------+---------+---------+---------+------1440
```

FIG. 2A-3

```
          E   A   E   K   Q   K   A   A   E   A   T   K   V   A   E   A   E   K   Q   K
         GAAGCGGAGAAGCAGAAGGCAGCTGAAGCCACGAAGGTTGCCGAAGCGGAGAAGCAGAAG
         ---------+---------+---------+---------+---------+------1500

A   A   E   A   T   K   V   A   E   A   E   K   Q   K   A   A   E   A   T   K
         GCAGCTGAAGCCACGAAGGTTGCCGAAGCGGAGAAGCAGAAGGCAGCTGAAGCCACGAAG
         ---------+---------+---------+---------+---------+------1560

V   A   E   A   E   K   Q   K   A   A   E   A   T   K   V   A   E   A   E   K
         GTTGCCGAAGCGGAGAAGCAGAAGGCAGCTGAAGCCACGAAGGTTGCCGAAGCGGAGAAG
         ---------+---------+---------+---------+---------+------1620

Q   K   A   A   E   A   T   K   V   A   E   A   E   K   Q   K   A   G   E   F
         CAGAAGGCAGCTGAAGCCACGAAGGTTGCCGAAGCGGAGAAGCAGAAGGCAGGGGAATTC
         ---------+---------+---------+---------+---------+------1680

I   V   T   D   *
         ATCGTGACTGACTGA
         ---------+-1695
```

FIG. 2B-1

```
      M   S   P   I   L   G   Y   W   K   I   K   G   L   V   Q   P   T   R   L   L
ATGTCCCCTATACTAGGTTATTGGAAAATTAAGGGCCTTGTGCAACCCACTCGACTTCTT
---------+---------+---------+---------+---------+---------+  60

L   E   Y   L   E   E   K   Y   E   E   H   L   Y   E   R   D   E   G   D   K
TTGGAATATCTTGAAGAAAAATATGAAGAGCATTTGTATGAGCGCGATGAAGGTGATAAA
---------+---------+---------+---------+---------+---------+  120

W   R   N   K   K   F   E   L   G   L   E   F   P   N   L   P   Y   Y   I   D
TGGCGAAACAAAAAGTTTGAATTGGGTTTGGAGTTTCCCAATCTTCCTTATTATATTGAT
---------+---------+---------+---------+---------+---------+  180

G   D   V   K   L   T   Q   S   M   A   I   I   R   Y   I   A   D   K   H   N
GGTGATGTTAAATTAACACAGTCTATGGCCATCATACGTTATATAGCTGACAAGCACAAC
---------+---------+---------+---------+---------+---------+  240

M   L   G   G   C   P   K   E   R   A   E   I   S   M   L   E   G   A   V   L
ATGTTGGGTGGTTGTCCAAAAGAGCGTGCAGAGATTTCAATGCTTGAAGGAGCGGTTTTG
---------+---------+---------+---------+---------+---------+  300

D   I   R   Y   G   V   S   R   I   A   Y   S   K   D   F   E   T   L   K   V
GATATTAGATACGGTGTTTCGAGAATTGCATATAGTAAAGACTTTGAAACTCTCAAAGTT
---------+---------+---------+---------+---------+---------+  360

D   F   L   S   K   L   P   E   M   L   K   M   F   E   D   R   L   C   H   K
GATTTTCTTAGCAAGCTACCTGAAATGCTGAAAATGTTCGAAGATCGTTTATGTCATAAA
---------+---------+---------+---------+---------+---------+  420

T   Y   L   N   G   D   H   V   T   H   P   D   F   M   L   Y   D   A   L   D
ACATATTTAAATGGTGATCATGTAACCCATCCTGACTTCATGTTGTATGACGCTCTTGAT
---------+---------+---------+---------+---------+---------+  480

V   V   L   Y   M   D   P   M   C   L   D   A   F   P   K   L   V   C   F   K
GTTGTTTTATACATGGACCCAATGTGCCTGGATGCGTTCCCAAAATTAGTTTGTTTTAAA
---------+---------+---------+---------+---------+---------+  540

K   R   I   E   A   I   P   Q   I   D   K   Y   L   K   S   S   K   Y   I   A
AAACGTATTGAAGCTATCCCACAAATTGATAAGTACTTGAAATCCAGCAAGTATATAGCA
---------+---------+---------+---------+---------+---------+  600

W   P   L   Q   G   W   Q   A   T   F   G   G   D   H   P   P   K   S   D
TGGCCTTTGCAGGGCTGGCAAGCCACGTTTGGTGGTGGCGACCATCCTCCAAAATCGGAT
---------+---------+---------+---------+---------+---------+  660

L   V   P   R   G   S   P   S   Q   L   Q   Q   A   E   N   N   I   T   N   S
CTGGTTCCGCGTGGATCCCCGTCCCAGCTCCAACAGGCAGAAAATAATATCACTAATTCC
---------+---------+---------+---------+---------+---------+  720
```

FIG. 2B-2

```
        K   K   E   M   T   K   L   R   E   K   V   K   K   A   E   K   E   K   L   D
     AAAAAAGAAATGACAAAGCTACGAGAAAAAGTGAAAAAGGCCGAGAAAGAAAAATTGGAC
     ---------+---------+---------+---------+---------+-------780

A   I   N   R   A   T   K   L   E   E   E   R   N   Q   A   Y   K   A   A   H
     GCCATTAACCGGGCAACCAAGCTGGAAGAGGAACGAAACCAAGCGTACAAAGCAGCACAC
     ---------+---------+---------+---------+---------+-------840

K   A   E   E   E   K   A   K   T   F   Q   R   L   I   T   F   E   S   E   N
     AAGGCAGAGGAGGAAAAGGCTAAAACATTTCAACGCCTTATAACATTTGAGTCGGAAAAT
     ---------+---------+---------+---------+---------+-------900

I   N   L   K   K   R   P   N   D   A   V   S   N   R   D   K   K   K   N   S
     ATTAACTTAAAGAAAAGGCCAAATGACGCAGTTTCAAATCGGGATAAGAAAAAAAATTCT
     ---------+---------+---------+---------+---------+-------960

E   T   A   K   T   D   E   V   E   K   Q   R   A   A   E   A   A   K   A   V
     GAAACCGCAAAAACTGACGAAGTAGAGAAACAGAGGGCGGCTGAGGCTGCCAAGGCCGTG
     ---------+---------+---------+---------+---------+-------1020

E   T   E   K   Q   R   A   G   E   F   I   V   T   D   *
     GAGACGGAGAAGCAGAGGGCAGGGGAATTCATCGTGACTGACTGA
     ---------+---------+---------+---------+-1065
```

FIG. 2C-1

```
  M   S   P   I   L   G   Y   W   K   I   K   G   L   V   Q   P   T   R   L   L
ATGTCCCCTATACTAGGTTATTGGAAAATTAAGGGCCTTGTGCAACCCACTCGACTTCTT
---------+---------+---------+---------+---------+---------60

L   E   Y   L   E   E   K   Y   E   E   H   L   Y   E   R   D   E   G   D   K
TTGGAATATCTTGAAGAAAAATATGAAGAGCATTTGTATGAGCGCGATGAAGGTGATAAA
---------+---------+---------+---------+---------+---------120

W   R   N   K   K   F   E   L   G   L   E   F   P   N   L   P   Y   Y   I   D
TGGCGAAACAAAAAGTTTGAATTGGGTTTGGAGTTTCCCAATCTTCCTTATTATATTGAT
---------+---------+---------+---------+---------+---------180

G   D   V   K   L   T   Q   S   M   A   I   I   R   Y   I   A   D   K   H   N
GGTGATGTTAAATTAACACAGTCTATGGCCATCATACGTTATATAGCTGACAAGCACAAC
---------+---------+---------+---------+---------+---------240

M   L   G   G   C   P   K   E   R   A   E   I   S   M   L   E   G   A   V   L
ATGTTGGGTGGTTGTCCAAAAGAGCGTGCAGAGATTTCAATGCTTGAAGGAGCGGTTTTG
---------+---------+---------+---------+---------+---------300

D   I   R   Y   G   V   S   R   I   A   Y   S   K   D   F   E   T   L   K   V
GATATTAGATACGGTGTTTCGAGAATTGCATATAGTAAAGACTTTGAAACTCTCAAAGTT
---------+---------+---------+---------+---------+---------360

D   F   L   S   K   L   P   E   M   L   K   M   F   E   D   R   L   C   H   K
GATTTTCTTAGCAAGCTACCTGAAATGCTGAAAATGTTCGAAGATCGTTTATGTCATAAA
---------+---------+---------+---------+---------+---------420

T   Y   L   N   G   D   H   V   T   H   P   D   F   M   L   Y   D   A   L   D
ACATATTTAAATGGTGATCATGTAACCCATCCTGACTTCATGTTGTATGACGCTCTTGAT
---------+---------+---------+---------+---------+---------480

V   V   L   Y   M   D   P   M   C   L   D   A   F   P   K   L   V   C   F   K
GTTGTTTTATACATGGACCCAATGTGCCTGGATGCGTTCCCAAAATTAGTTTGTTTTAAA
---------+---------+---------+---------+---------+---------540

K   R   I   E   A   I   P   Q   I   D   K   Y   L   K   S   S   K   Y   I   A
AAACGTATTGAAGCTATCCCACAAATTGATAAGTACTTGAAATCCAGCAAGTATATAGCA
---------+---------+---------+---------+---------+---------600

W   P   L   Q   G   W   Q   A   T   F   G   G   G   D   H   P   P   K   S   D
TGGCCTTTGCAGGGCTGGCAAGCCACGTTTGGTGGTGGCGACCATCCTCCAAAATCGGAT
---------+---------+---------+---------+---------+---------660

P   A   E   A   A   K   A   M   E   S   Q   K   Q   R   F   L   E   R   F   A
CCCCCTGAAGCTGCCAAGGCTATGGAGTCGCAGAAGCAGAGATTCTTAGAACGTTTTGCG
---------+---------+---------+---------+---------+---------720
```

FIG. 2C-2

```
          V   L   E   E   E   K   K   A   A   L   R   A   A   A   E   M   E   R   R   K   I
     GTTCTTGAGGAGGAGAAAAAGGCAGCCTTAAGAGCGGCGGAGATGGAGAGGAGGAAAATA
     ---------+---------+---------+---------+---------+-------780

T   N   I   M   K   N   K   G   V   R   S   S   D   S   V   P   L   V   E   G
     ACAAACATAATGAAGAATAAAGGTGTACGCAGTTCGGATTCGGTGCCGCTTGTGGAGGGG
     ---------+---------+---------+---------+---------+-------840

N   R   S   V   T   E   S   S   C   R   N   R   F   R   F   C   R   N   R   F
     AATCGCTCTGTTACTGAGAGTTCTTGTAGAAATCGGTTTCGTTTTTGTAGAAATCGGTTT
     ---------+---------+---------+---------+---------+-------900

R   F   S   C   S   V   M   *
     CGTTTTTCATGTTCTGTAATGTGA
     ---------+---------+-924
```

FIG. 2D-1

```
  M   S   P   I   L   G   Y   W   K   I   K   G   L   V   Q   P   T   R   L   L
ATGTCCCCTATACTAGGTTATTGGAAAATTAAGGGCCTTGTGCAACCCACTCGACTTCTT
---------+---------+---------+---------+---------+--------60

L   E   Y   L   E   E   K   Y   E   E   H   L   Y   E   R   D   E   G   D   K
TTGGAATATCTTGAAGAAAAATATGAAGAGCATTTGTATGAGCGCGATGAAGGTGATAAA
---------+---------+---------+---------+---------+--------120

W   R   N   K   K   F   E   L   G   L   E   F   P   N   L   P   Y   Y   I   D
TGGCGAAACAAAAAGTTTGAATTGGGTTTGGAGTTTCCCAATCTTCCTTATTATATTGAT
---------+---------+---------+---------+---------+--------180

G   D   V   K   L   T   Q   S   M   A   I   I   R   Y   I   A   D   K   H   N
GGTGATGTTAAATTAACACAGTCTATGGCCATCATACGTTATATAGCTGACAAGCACAAC
---------+---------+---------+---------+---------+--------240

M   L   G   G   C   P   K   E   R   A   E   I   S   M   L   E   G   A   V   L
ATGTTGGGTGGTTGTCCAAAAGAGCGTGCAGAGATTTCAATGCTTGAAGGAGCGGTTTTG
---------+---------+---------+---------+---------+--------300

D   I   R   Y   G   V   S   R   I   A   Y   S   K   D   F   E   T   L   K   V
GATATTAGATACGGTGTTTCGAGAATTGCATATAGTAAAGACTTTGAAACTCTCAAAGTT
---------+---------+---------+---------+---------+--------360

D   F   L   S   K   L   P   E   M   L   K   M   F   E   D   R   L   C   H   K
GATTTTCTTAGCAAGCTACCTGAAATGCTGAAAATGTTCGAAGATCGTTTATGTCATAAA
---------+---------+---------+---------+---------+--------420

T   Y   L   N   G   D   H   V   T   H   P   D   F   M   L   Y   D   A   L   D
ACATATTTAAATGGTGATCATGTAACCCATCCTGACTTCATGTTGTATGACGCTCTTGAT
---------+---------+---------+---------+---------+--------480

V   V   L   Y   M   D   P   M   C   L   D   A   F   P   K   L   V   C   F   K
GTTGTTTTATACATGGACCCAATGTGCCTGGATGCGTTCCCAAAATTAGTTTGTTTTAAA
---------+---------+---------+---------+---------+--------540

K   R   I   E   A   I   P   Q   I   D   K   Y   L   K   S   S   K   Y   I   A
AAACGTATTGAAGCTATCCCACAAATTGATAAGTACTTGAAATCCAGCAAGTATATAGCA
---------+---------+---------+---------+---------+--------600

W   P   L   Q   G   W   Q   A   T   F   G   G   G   D   H   P   P   K   S   D
TGGCCTTTGCAGGGCTGGCAAGCCACGTTTGGTGGTGGCGACCATCCTCCAAAATCGGAT
---------+---------+---------+---------+---------+--------660

L   V   P   R   G   S   P   S   Q   L   Q   Q   A   E   N   N   I   T   N   S
CTGGTTCCGCGTGGATCCCCGTCCCAGCTCCAACAGGCAGAAAATAATATCACTAATTCC
---------+---------+---------+---------+---------+--------720
```

FIG. 2D-2

```
      K   K   E   M   T   K   L   R   E   K   V   K   K   A   E   K   E   K   L   D
   AAAAAAGAAATGACAAAGCTACGAGAAAAAGTGAAAAAGGCCGAGAAAGAAAAATTGGAC
   ---------+---------+---------+---------+---------+---------+------780

A   I   N   R   A   T   K   L   E   E   E   R   N   Q   A   Y   K   A   A   H
   GCCATTAACCGGGCAACCAAGCTGGAAGAGGAACGAAACCAAGCGTACAAAGCAGCACAC
   ---------+---------+---------+---------+---------+---------+------840

K   A   E   E   E   K   A   K   T   F   Q   R   L   I   T   F   E   S   E   N
   AAGGCAGAGGAGGAAAAGGCTAAAACATTTCAACGCCTTATAACATTTGAGTCGGAAAAT
   ---------+---------+---------+---------+---------+---------+------900

I   N   L   K   K   R   P   N   D   A   V   S   N   R   D   K   K   K   N   S
   ATTAACTTAAAGAAAAGGCCAAATGACGCAGTTTCAAATCGGGATAAGAAAAAAAATTCT
   ---------+---------+---------+---------+---------+---------+------960

E   T   A   K   T   D   E   V   E   K   Q   R   A   A   E   A   A   K   A   V
   GAAACCGCAAAAACTGACGAAGTAGAGAAACAGAGGGCGGCTGAGGCTGCCAAGGCCGTG
   ---------+---------+---------+---------+---------+---------+------1020

E   T   E   K   Q   R   A   A   E   A   T   K   V   A   E   A   E   K   R   K
   GAGACGGAGAAGCAGAGGGCAGCTGAGGCCACGAAGGTTGCCGAAGCGGAGAAGCGGAAG
   ---------+---------+---------+---------+---------+---------+------1080

A   A   E   A   A   K   A   V   E   T   E   K   Q   R   A   A   E   A   T   K
   GCAGCTGAGGCCGCCAAGGCCGTGGAGACGGAGAAGCAGAGGGCAGCTGAAGCCACGAAG
   ---------+---------+---------+---------+---------+---------+------1140

V   A   E   A   E   K   Q   K   A   A   E   A   A   K   A   V   E   T   E   K
   GTTGCCGAAGCGGAGAAGCAGAAGGCAGCTGAGGCCGCCAAGGCCGTGGAGACGGAGAAG
   ---------+---------+---------+---------+---------+---------+------1200

Q   R   A   A   E   A   T   K   V   A   E   A   E   K   Q   R   A   A   E   A
   CAGAGGGCAGCTGAAGCCACGAAGGTTGCCGAAGCGGAGAAGCAGAGGGCAGCTGAAGCC
   ---------+---------+---------+---------+---------+---------+------1260

M   K   V   A   E   A   E   K   Q   K   A   A   E   A   T   K   V   A   E   A
   ATGAAGGTTGCCGAAGCGGAGAAGCAGAAGGCAGCTGAGGCCACGAAGGTTGCCGAAGCG
   ---------+---------+---------+---------+---------+---------+------1320

E   K   Q   K   A   A   E   A   T   K   V   A   E   A   E   K   Q   K   A   A
   GAGAAGCAGAAGGCAGCTGAAGCCACGAAGGTTGCCGAAGCGGAGAAGCAGAAGGCAGCT
   ---------+---------+---------+---------+---------+---------+------1380

E   A   T   K   V   A   E   A   E   K   Q   K   A   A   E   A   T   K   V   A
   GAAGCCACGAAGGTTGCCGAAGCGGAGAAGCAGAAGGCAGCTGAAGCCACGAAGGTTGCC
   ---------+---------+---------+---------+---------+---------+------1440
```

FIG. 2D-3

```
        E   A   E   K   Q   K   A   A   E   A   T   K   V   A   E   A   E   K   Q   K
        GAAGCGGAGAAGCAGAAGGCAGCTGAAGCCACGAAGGTTGCCGAAGCGGAGAAGCAGAAG
        ---------+---------+---------+---------+---------+------1500

A   A   E   A   T   K   V   A   E   A   E   K   Q   K   A   A   E   A   T   K
        GCAGCTGAAGCCACGAAGGTTGCCGAAGCGGAGAAGCAGAAGGCAGCTGAAGCCACGAAG
        ---------+---------+---------+---------+---------+------1560

V   A   E   A   E   K   Q   K   A   A   E   A   T   K   V   A   E   A   E   K
        GTTGCCGAAGCGGAGAAGCAGAAGGCAGCTGAAGCCACGAAGGTTGCCGAAGCGGAGAAG
        ---------+---------+---------+---------+---------+------1620

Q   K   A   A   E   A   T   K   V   A   E   A   E   K   Q   K   A   A   E   A
        CAGAAGGCAGCTGAAGCCACGAAGGTTGCCGAAGCGGAGAAGCAGAAGGCAGCTGAAGCT
        ---------+---------+---------+---------+---------+------1680

A   K   A   M   E   S   Q   K   Q   R   F   L   E   R   F   A   V   L   E   E
        GCCAAGGCTATGGAGTCGCAGAAGCAGAGATTCTTAGAACGTTTTGCGGTTCTTGAGGAG
        ---------+---------+---------+---------+---------+------1740

E   K   K   A   A   L   R   A   A   E   M   E   R   R   K   I   T   N   I   M
        GAGAAAAAGGCAGCCTTAAGAGCGGCGGAGATGGAGAGGAGGAAAATAACAAACATAATG
        ---------+---------+---------+---------+---------+------1800

K   N   K   G   V   R   S   S   D   S   V   P   L   V   E   G   N   R   S   V
        AAGAATAAAGGTGTACGCAGTTCGGATTCGGTGCCGCTTGTGGAGGGGAATCGCTCTGTT
        ---------+---------+---------+---------+---------+------1860

T   E   S   S   C   R   N   R   F   R   F   C   R   N   R   F   R   F   S   C
        ACTGAGAGTTCTTGTAGAAATCGGTTTCGTTTTTGTAGAAATCGGTTTCGTTTTTCATGT
        ---------+---------+---------+---------+---------+------1920

S   V   M   *
        TCTGTAATGTGA
        --------1932
```

FIG. 2E-1

```
      M   S   P   I   L   G   Y   W   K   I   K   G   L   V   Q   P   T   R   L   L
     ATGTCCCCTATACTAGGTTATTGGAAAATTAAGGGCCTTGTGCAACCCACTCGACTTCTT
     ---------+---------+---------+---------+---------+--------60

L   E   Y   L   E   E   K   Y   E   E   H   L   Y   E   R   D   E   G   D   K
     TTGGAATATCTTGAAGAAAAATATGAAGAGCATTTGTATGAGCGCGATGAAGGTGATAAA
     ---------+---------+---------+---------+---------+-------120

W   R   N   K   K   F   E   L   G   L   E   F   P   N   L   P   Y   Y   I   D
     TGGCGAAACAAAAAGTTTGAATTGGGTTTGGAGTTTCCCAATCTTCCTTATTATATTGAT
     ---------+---------+---------+---------+---------+-------180

G   D   V   K   L   T   Q   S   M   A   I   I   R   Y   I   A   D   K   H   N
     GGTGATGTTAAATTAACACAGTCTATGGCCATCATACGTTATATAGCTGACAAGCACAAC
     ---------+---------+---------+---------+---------+-------240

M   L   G   G   C   P   K   E   R   A   E   I   S   M   L   E   G   A   V   L
     ATGTTGGGTGGTTGTCCAAAAGAGCGTGCAGAGATTTCAATGCTTGAAGGAGCGGTTTTG
     ---------+---------+---------+---------+---------+-------300

D   I   R   Y   G   V   S   R   I   A   Y   S   K   D   F   E   T   L   K   V
     GATATTAGATACGGTGTTTCGAGAATTGCATATAGTAAAGACTTTGAAACTCTCAAAGTT
     ---------+---------+---------+---------+---------+-------360

D   F   L   S   K   L   P   E   M   L   K   M   F   E   D   R   L   C   H   K
     GATTTTCTTAGCAAGCTACCTGAAATGCTGAAAATGTTCGAAGATCGTTTATGTCATAAA
     ---------+---------+---------+---------+---------+-------420

T   Y   L   N   G   D   H   V   T   H   P   D   F   M   L   Y   D   A   L   D
     ACATATTTAAATGGTGATCATGTAACCCATCCTGACTTCATGTTGTATGACGCTCTTGAT
     ---------+---------+---------+---------+---------+-------480

V   V   L   Y   M   D   P   M   C   L   D   A   F   P   K   L   V   C   F   K
     GTTGTTTTATACATGGACCCAATGTGCCTGGATGCGTTCCCAAAATTAGTTTGTTTTAAA
     ---------+---------+---------+---------+---------+-------540

K   R   I   E   A   I   P   Q   I   D   K   Y   L   K   S   S   K   Y   I   A
     AAACGTATTGAAGCTATCCCACAAATTGATAAGTACTTGAAATCCAGCAAGTATATAGCA
     ---------+---------+---------+---------+---------+-------600

W   P   L   Q   G   W   Q   A   T   F   G   G   G   D   H   P   P   K   S   D
     TGGCCTTTGCAGGGCTGGCAAGCCACGTTTGGTGGTGGCGACCATCCTCCAAAATCGGAT
     ---------+---------+---------+---------+---------+-------660

L   I   E   G   R   G   I   P   P   G   C   R   N   S   T   K   V   A   E   A
     CTGATCGAAGGTCGTGGGATCCCCCCGGGCTGCAGGAATTCCACGAAGGTTGCCGAAGCG
     ---------+---------+---------+---------+---------+-------720
```

FIG. 2E-2

```
         E   K   Q   K   A   A   E   A   T   K   V   A   E   A   E   K   Q   R   A   A
        GAGAAGCAGAAGGCAGCTGAAGCCACGAAGGTTGCCGAAGCGGAGAAGCAGAGGGCAGCT
        ---------+---------+---------+---------+---------+-------780

E   A   T   K   V   A   E   A   E   K   Q   K   A   A   E   A   T   K   V   A
        GAAGCCACGAAGGTTGCCGAAGCGGAGAAGCAGAAGGCAGCTGAAGCCACGAAGGTTGCC
        ---------+---------+---------+---------+---------+-------840

E   A   E   K   Q   R   A   A   E   A   T   K   V   A   E   A   E   K   Q   K
        GAAGCGGAGAAGCAGAGGGCAGCTGAAGCCACGAAGGTTGCCGAAGCGGAGAAGCAAAAG
        ---------+---------+---------+---------+---------+-------900

A   A   E   A   T   K   V   A   G   D   E   K   Q   K   A   A   E   A   T   K
        GCAGCTGAGGCCACGAAGGTTGCCGGAGACGAGAAGCAGAAGGCAGCTGAAGCCACGAAG
        ---------+---------+---------+---------+---------+-------960

V   A   E   A   E   K   Q   K   A   A   E   A   T   K   V   A   E   A   E   K
        GTTGCCGAAGCGGAGAAGCAGAAGGCAGCTGAAGCCACGAAGGTTGCCGAAGCGGAGAAG
        ---------+---------+---------+---------+---------+-------1020

Q   K   A   A   E   A   T   K   V   A   E   A   E   K   Q   K   A   A   E   A
        CAGAAGGCAGCTGAAGCCACGAAGGTTGCCGAAGCGGAGAAGCAGAAGGCAGCTGAAGCC
        ---------+---------+---------+---------+---------+-------1080

T   K   V   A   E   A   E   K   Q   K   A   A   E   A   T   K   V   A   E   A
        ACGAAGGTTGCCGAAGCGGAGAAGCAGAAGGCAGCTGAAGCCACGAAGGTTGCCGAAGCG
        ---------+---------+---------+---------+---------+-------1140

E   K   Q   K   A   A   E   A   T   K   V   A   E   A   E   K   Q   K   A   A
        GAGAAGCAGAAGGCAGCTGAAGCCACGAAGGTTGCCGAAGCGGAGAAGCAGAAGGCAGCT
        ---------+---------+---------+---------+---------+-------1200

E   A   T   K   V   A   E   A   E   K   Q   K   A   A   E   A   T   K   V   A
        GAAGCCACGAAGGTTGCCGAAGCGGAGAAGCAGAAGGCAGCTGAAGCCACGAAGGTTGCC
        ---------+---------+---------+---------+---------+-------1260

E   A   E   K   Q   K   A   A   E   A   T   K   V   A   E   A   E   K   Q   K
        GAAGCGGAGAAGCAGAAGGCAGCTGAAGCCACGAAGGTTGCCGAAGCGGAGAAGCAGAAG
        ---------+---------+---------+---------+---------+-------1320

A   A   E   A   T   K   V   A   E   A   E   K   Q   K   V   G   E   A   D   Q
        GCAGCTGAAGCCACGAAGGTTGCCGAAGCGGAGAAGCAGAAGGTAGGTGAGGCTGATCAA
        ---------+---------+---------+---------+---------+-------1380

A   Y   R   Y   R   R   E   F   I   V   T   D   *
        GCTTATCGATACCGTCGGGAATTCATCGTGACTGACTGA
        ---------+---------+---------+-----1419
```

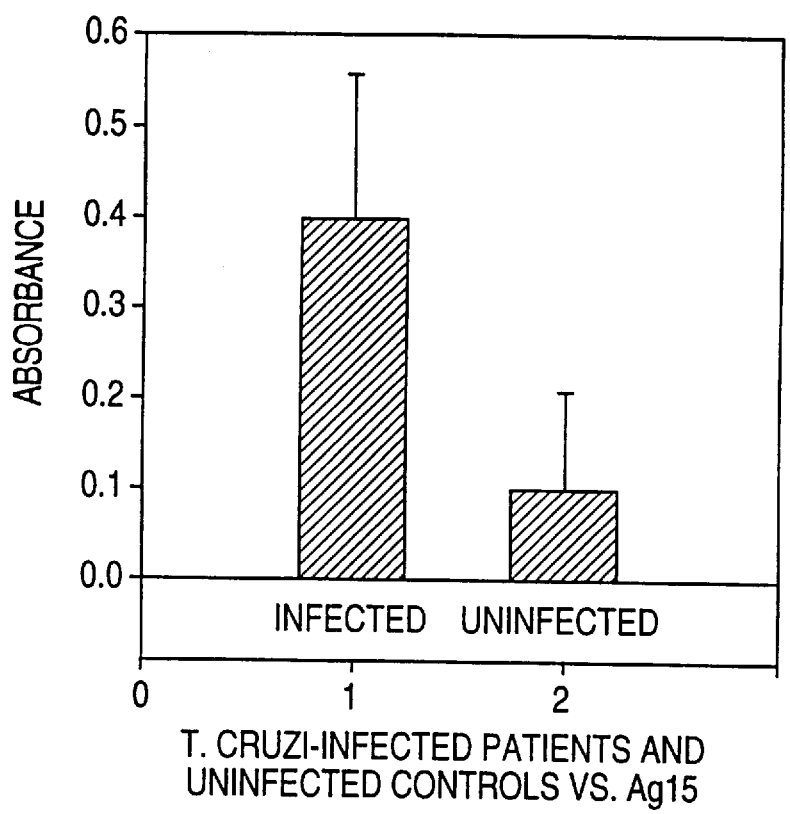

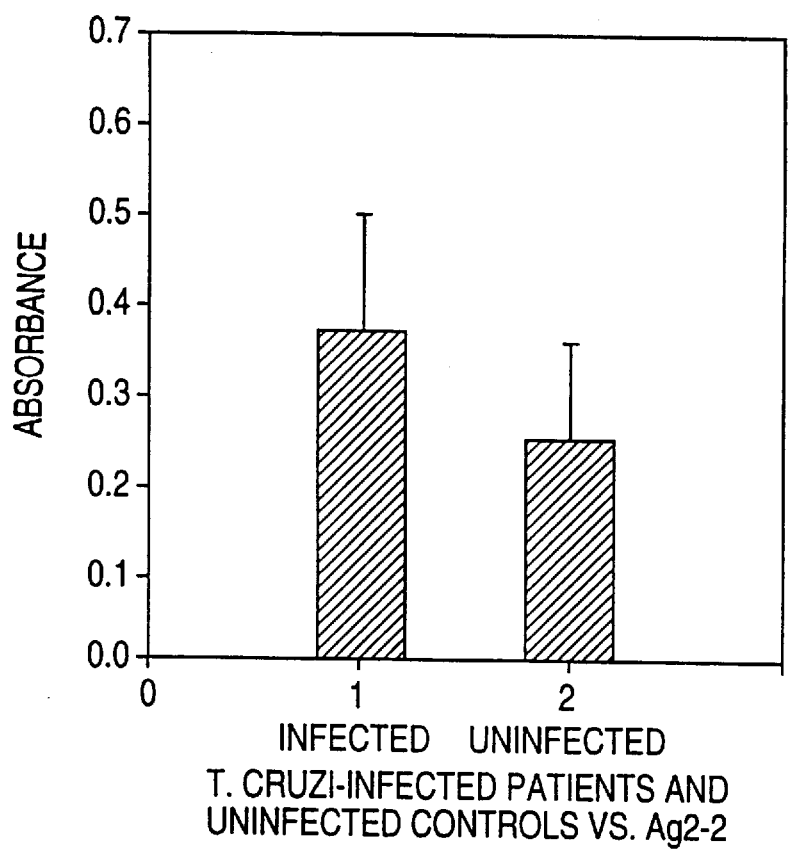

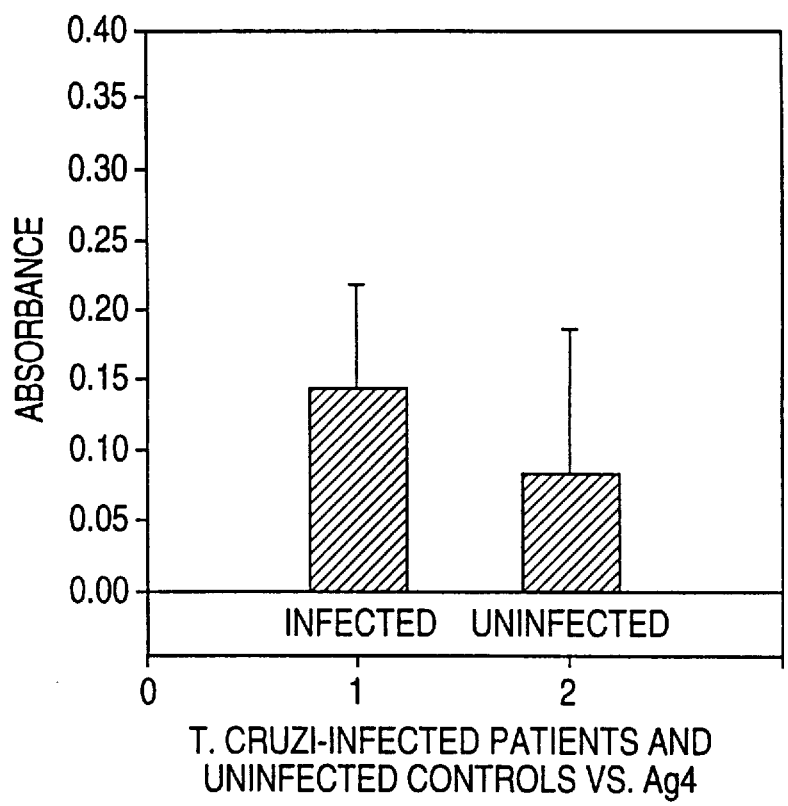

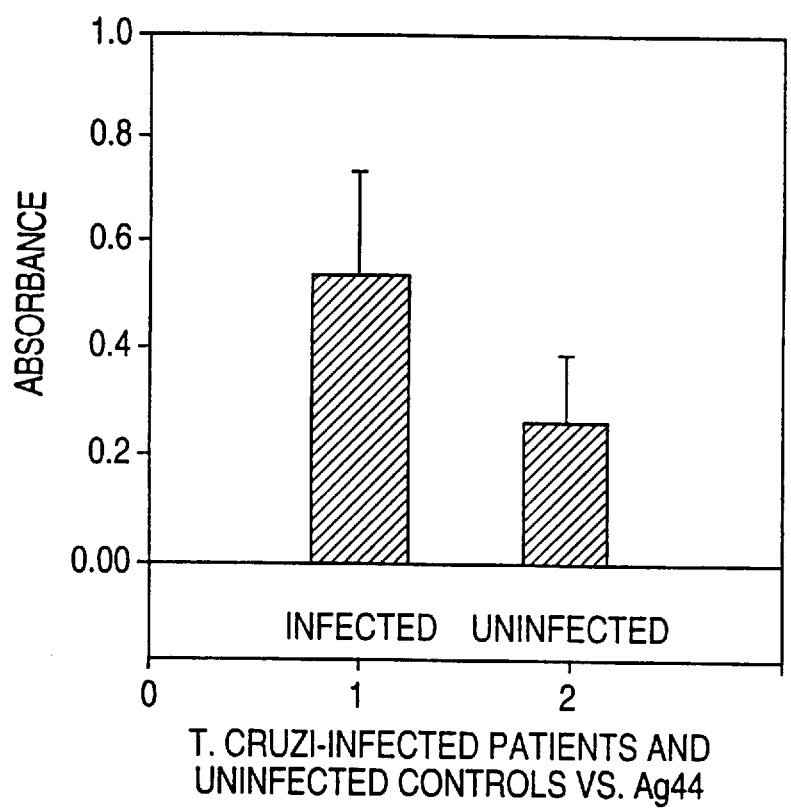

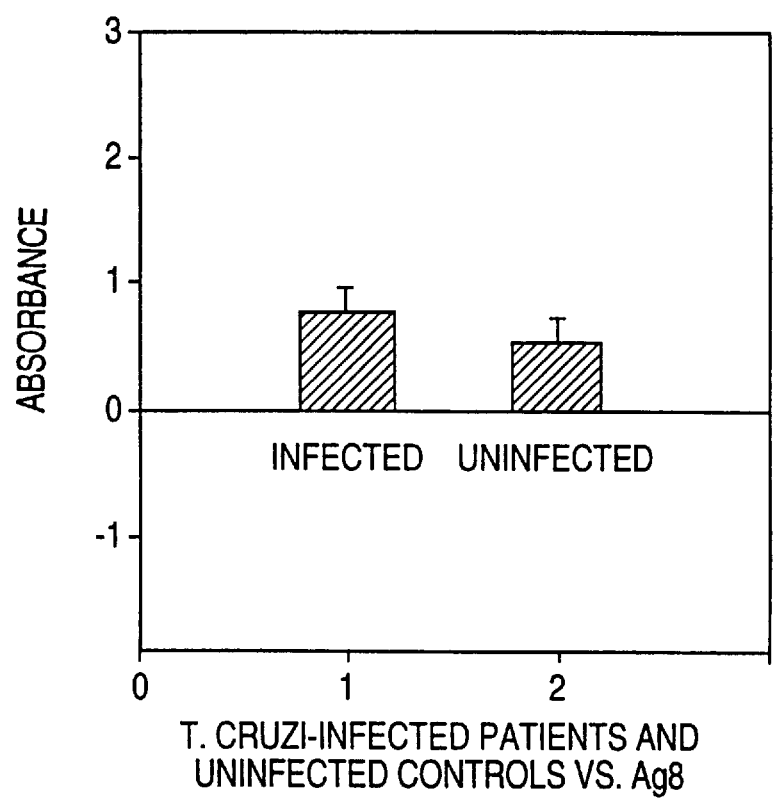

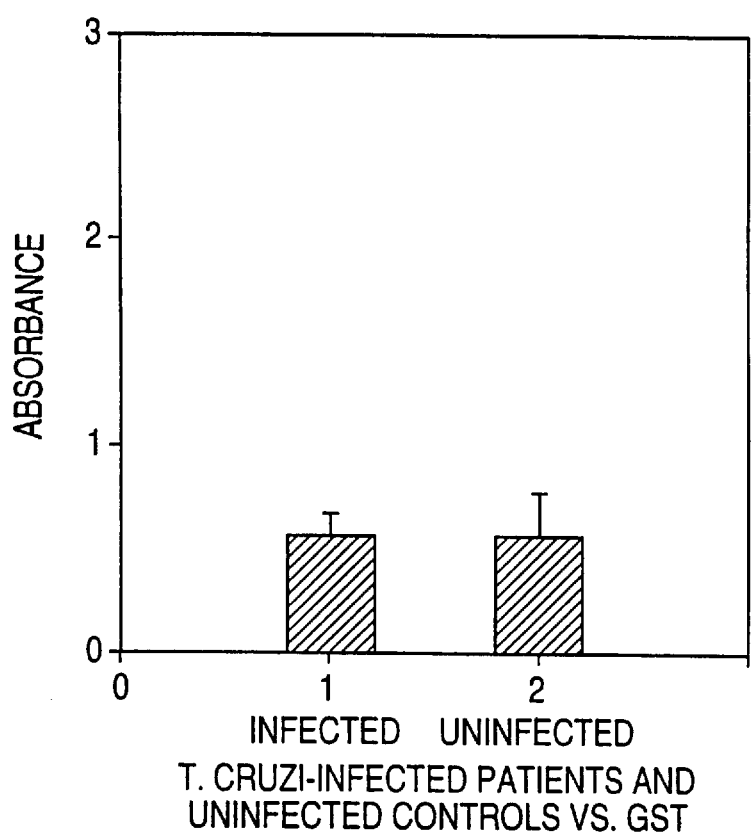

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1695 base pairs
        ( B ) TYPE: nucleic acid
        ( C ) STRANDEDNESS: double -continued ( D ) TOPOLOGY: linear ( i i ) MOLECULE TYPE: DNA (genomic)

( i x ) FEATURE:
    ( A ) NAME/KEY: CDS
    ( B ) LOCATION: 1..1692

( x i ) SEQUENCE DESCRIPTION: SEQ ID NO:1:

```
ATG TCC CCT ATA CTA GGT TAT TGG AAA ATT AAG GGC CTT GTG CAA CCC        48
Met Ser Pro Ile Leu Gly Tyr Trp Lys Ile Lys Gly Leu Val Gln Pro
 1           5                  10                  15

ACT CGA CTT CTT TTG GAA TAT CTT GAA GAA AAA TAT GAA GAG CAT TTG        96
Thr Arg Leu Leu Leu Glu Tyr Leu Glu Glu Lys Tyr Glu Glu His Leu
             20                  25                  30

TAT GAG CGC GAT GAA GGT GAT AAA TGG CGA AAC AAA AAG TTT GAA TTG       144
Tyr Glu Arg Asp Glu Gly Asp Lys Trp Arg Asn Lys Lys Phe Glu Leu
         35                  40                  45

GGT TTG GAG TTT CCC AAT CTT CCT TAT TAT ATT GAT GGT GAT GTT AAA       192
Gly Leu Glu Phe Pro Asn Leu Pro Tyr Tyr Ile Asp Gly Asp Val Lys
 50                  55                  60

TTA ACA CAG TCT ATG GCC ATC ATA CGT TAT ATA GCT GAC AAG CAC AAC       240
Leu Thr Gln Ser Met Ala Ile Ile Arg Tyr Ile Ala Asp Lys His Asn
 65                  70                  75                  80

ATG TTG GGT GGT TGT CCA AAA GAG CGT GCA GAG ATT TCA ATG CTT GAA       288
Met Leu Gly Gly Cys Pro Lys Glu Arg Ala Glu Ile Ser Met Leu Glu
                 85                  90                  95

GGA GCG GTT TTG GAT ATT AGA TAC GGT GTT TCG AGA ATT GCA TAT AGT       336
Gly Ala Val Leu Asp Ile Arg Tyr Gly Val Ser Arg Ile Ala Tyr Ser
            100                 105                 110

AAA GAC TTT GAA ACT CTC AAA GTT GAT TTT CTT AGC AAG CTA CCT GAA       384
Lys Asp Phe Glu Thr Leu Lys Val Asp Phe Leu Ser Lys Leu Pro Glu
        115                 120                 125

ATG CTG AAA ATG TTC GAA GAT CGT TTA TGT CAT AAA ACA TAT TTA AAT       432
Met Leu Lys Met Phe Glu Asp Arg Leu Cys His Lys Thr Tyr Leu Asn
    130                 135                 140

GGT GAT CAT GTA ACC CAT CCT GAC TTC ATG TTG TAT GAC GCT CTT GAT       480
Gly Asp His Val Thr His Pro Asp Phe Met Leu Tyr Asp Ala Leu Asp
145                 150                 155                 160

GTT GTT TTA TAC ATG GAC CCA ATG TGC CTG GAT GCG TTC CCA AAA TTA       528
Val Val Leu Tyr Met Asp Pro Met Cys Leu Asp Ala Phe Pro Lys Leu
                165                 170                 175

GTT TGT TTT AAA AAA CGT ATT GAA GCT ATC CCA CAA ATT GAT AAG TAC       576
Val Cys Phe Lys Lys Arg Ile Glu Ala Ile Pro Gln Ile Asp Lys Tyr
            180                 185                 190

TTG AAA TCC AGC AAG TAT ATA GCA TGG CCT TTG CAG GGC TGG CAA GCC       624
Leu Lys Ser Ser Lys Tyr Ile Ala Trp Pro Leu Gln Gly Trp Gln Ala
        195                 200                 205

ACG TTT GGT GGT GGC GAC CAT CCT CCA AAA TCG GAT CTG GTT CCG CGT       672
Thr Phe Gly Gly Gly Asp His Pro Pro Lys Ser Asp Leu Val Pro Arg
    210                 215                 220

GGA TCC CCG TCC CAG CTC CAA CAG GCA GAA AAT AAT ATC ACT AAT TCC       720
Gly Ser Pro Ser Gln Leu Gln Gln Ala Glu Asn Asn Ile Thr Asn Ser
225                 230                 235                 240

AAA AAA GAA ATG ACA AAG CTA CGA GAA AAA GTG AAA AAG GCC GAG AAA       768
Lys Lys Glu Met Thr Lys Leu Arg Glu Lys Val Lys Lys Ala Glu Lys
                245                 250                 255

GAA AAA TTG GAC GCC ATT AAC CGG GCA ACC AAG CTG GAA GAG GAA CGA       816
Glu Lys Leu Asp Ala Ile Asn Arg Ala Thr Lys Leu Glu Glu Glu Arg
            260                 265                 270

AAC CAA GCG TAC AAA GCA GCA CAC AAG GCA GAG GAG GAA AAG GCT AAA       864
Asn Gln Ala Tyr Lys Ala Ala His Lys Ala Glu Glu Glu Lys Ala Lys
```

|     |     |     |     |     | 275 |     |     |     | 280 |     |     |     |     | 285 |     |     |     |      |
|-----|-----|-----|-----|-----|-----|-----|-----|-----|-----|-----|-----|-----|-----|-----|-----|-----|-----|------|
| ACA | TTT | CAA | CGC | CTT | ATA | ACA | TTT | GAG | TCG | GAA | AAT | ATT | AAC | TTA | AAG |     |     | 912  |
| Thr | Phe | Gln | Arg | Leu | Ile | Thr | Phe | Glu | Ser | Glu | Asn | Ile | Asn | Leu | Lys |     |     |      |
|     | 290 |     |     |     |     | 295 |     |     |     | 300 |     |     |     |     |     |     |     |      |

| AAA | AGG | CCA | AAT | GAC | GCA | GTT | TCA | AAT | CGG | GAT | AAG | AAA | AAA | AAT | TCT | 960 |
|-----|-----|-----|-----|-----|-----|-----|-----|-----|-----|-----|-----|-----|-----|-----|-----|-----|
| Lys | Arg | Pro | Asn | Asp | Ala | Val | Ser | Asn | Arg | Asp | Lys | Lys | Lys | Asn | Ser |     |
| 305 |     |     |     | 310 |     |     |     |     | 315 |     |     |     |     | 320 |     |     |

| GAA | ACC | GCA | AAA | ACT | GAC | GAA | GTA | GAG | AAA | CAG | AGG | GCG | GCT | GAG | GCT | 1008 |
|-----|-----|-----|-----|-----|-----|-----|-----|-----|-----|-----|-----|-----|-----|-----|-----|------|
| Glu | Thr | Ala | Lys | Thr | Asp | Glu | Val | Glu | Lys | Gln | Arg | Ala | Ala | Glu | Ala |      |
|     |     |     |     | 325 |     |     |     |     | 330 |     |     |     |     | 335 |     |      |

| GCC | AAG | GCC | GTG | GAG | ACG | GAG | AAG | CAG | AGG | GCA | GCT | GAG | GCC | ACG | AAG | 1056 |
|-----|-----|-----|-----|-----|-----|-----|-----|-----|-----|-----|-----|-----|-----|-----|-----|------|
| Ala | Lys | Ala | Val | Glu | Thr | Glu | Lys | Gln | Arg | Ala | Ala | Glu | Ala | Thr | Lys |      |
|     |     |     | 340 |     |     |     |     | 345 |     |     |     |     | 350 |     |     |      |

| GTT | GCC | GAA | GCG | GAG | AAG | CGG | AAG | GCA | GCT | GAG | GCC | GCC | AAG | GCC | GTG | 1104 |
|-----|-----|-----|-----|-----|-----|-----|-----|-----|-----|-----|-----|-----|-----|-----|-----|------|
| Val | Ala | Glu | Ala | Glu | Lys | Arg | Lys | Ala | Ala | Glu | Ala | Ala | Lys | Ala | Val |      |
|     |     | 355 |     |     |     |     | 360 |     |     |     |     | 365 |     |     |     |      |

| GAG | ACG | GAG | AAG | CAG | AGG | GCA | GCT | GAA | GCC | ACG | AAG | GTT | GCC | GAA | GCG | 1152 |
|-----|-----|-----|-----|-----|-----|-----|-----|-----|-----|-----|-----|-----|-----|-----|-----|------|
| Glu | Thr | Glu | Lys | Gln | Arg | Ala | Ala | Glu | Ala | Thr | Lys | Val | Ala | Glu | Ala |      |
|     | 370 |     |     |     |     | 375 |     |     |     |     | 380 |     |     |     |     |      |

| GAG | AAG | CAG | AAG | GCA | GCT | GAG | GCC | GCC | AAG | GCC | GTG | GAG | ACG | GAG | AAG | 1200 |
|-----|-----|-----|-----|-----|-----|-----|-----|-----|-----|-----|-----|-----|-----|-----|-----|------|
| Glu | Lys | Gln | Lys | Ala | Ala | Glu | Ala | Ala | Lys | Ala | Val | Glu | Thr | Glu | Lys |      |
| 385 |     |     |     |     | 390 |     |     |     |     | 395 |     |     |     |     | 400 |      |

| CAG | AGG | GCA | GCT | GAA | GCC | ACG | AAG | GTT | GCC | GAA | GCG | GAG | AAG | CAG | AGG | 1248 |
|-----|-----|-----|-----|-----|-----|-----|-----|-----|-----|-----|-----|-----|-----|-----|-----|------|
| Gln | Arg | Ala | Ala | Glu | Ala | Thr | Lys | Val | Ala | Glu | Ala | Glu | Lys | Gln | Arg |      |
|     |     |     |     | 405 |     |     |     |     | 410 |     |     |     |     | 415 |     |      |

| GCA | GCT | GAA | GCC | ATG | AAG | GTT | GCC | GAA | GCG | GAG | AAG | CAG | AAG | GCA | GCT | 1296 |
|-----|-----|-----|-----|-----|-----|-----|-----|-----|-----|-----|-----|-----|-----|-----|-----|------|
| Ala | Ala | Glu | Ala | Met | Lys | Val | Ala | Glu | Ala | Glu | Lys | Gln | Lys | Ala | Ala |      |
|     |     |     | 420 |     |     |     |     | 425 |     |     |     |     | 430 |     |     |      |

| GAG | GCC | ACG | AAG | GTT | GCC | GAA | GCG | GAG | AAG | CAG | AAG | GCA | GCT | GAA | GCC | 1344 |
|-----|-----|-----|-----|-----|-----|-----|-----|-----|-----|-----|-----|-----|-----|-----|-----|------|
| Glu | Ala | Thr | Lys | Val | Ala | Glu | Ala | Glu | Lys | Gln | Lys | Ala | Ala | Glu | Ala |      |
|     |     | 435 |     |     |     |     | 440 |     |     |     |     | 445 |     |     |     |      |

| ACG | AAG | GTT | GCC | GAA | GCG | GAG | AAG | CAG | AAG | GCA | GCT | GAA | GCC | ACG | AAG | 1392 |
|-----|-----|-----|-----|-----|-----|-----|-----|-----|-----|-----|-----|-----|-----|-----|-----|------|
| Thr | Lys | Val | Ala | Glu | Ala | Glu | Lys | Gln | Lys | Ala | Ala | Glu | Ala | Thr | Lys |      |
|     | 450 |     |     |     |     | 455 |     |     |     |     | 460 |     |     |     |     |      |

| GTT | GCC | GAA | GCG | GAG | AAG | CAG | AAG | GCA | GCT | GAA | GCC | ACG | AAG | GTT | GCC | 1440 |
|-----|-----|-----|-----|-----|-----|-----|-----|-----|-----|-----|-----|-----|-----|-----|-----|------|
| Val | Ala | Glu | Ala | Glu | Lys | Gln | Lys | Ala | Ala | Glu | Ala | Thr | Lys | Val | Ala |      |
| 465 |     |     |     |     | 470 |     |     |     |     | 475 |     |     |     |     | 480 |      |

| GAA | GCG | GAG | AAG | CAG | AAG | GCA | GCT | GAA | GCC | ACG | AAG | GTT | GCC | GAA | GCG | 1488 |
|-----|-----|-----|-----|-----|-----|-----|-----|-----|-----|-----|-----|-----|-----|-----|-----|------|
| Glu | Ala | Glu | Lys | Gln | Lys | Ala | Ala | Glu | Ala | Thr | Lys | Val | Ala | Glu | Ala |      |
|     |     |     |     | 485 |     |     |     |     | 490 |     |     |     |     | 495 |     |      |

| GAG | AAG | CAG | AAG | GCA | GCT | GAA | GCC | ACG | AAG | GTT | GCC | GAA | GCG | GAG | AAG | 1536 |
|-----|-----|-----|-----|-----|-----|-----|-----|-----|-----|-----|-----|-----|-----|-----|-----|------|
| Glu | Lys | Gln | Lys | Ala | Ala | Glu | Ala | Thr | Lys | Val | Ala | Glu | Ala | Glu | Lys |      |
|     |     |     | 500 |     |     |     |     | 505 |     |     |     |     | 510 |     |     |      |

| CAG | AAG | GCA | GCT | GAA | GCC | ACG | AAG | GTT | GCC | GAA | GCG | GAG | AAG | CAG | AAG | 1584 |
|-----|-----|-----|-----|-----|-----|-----|-----|-----|-----|-----|-----|-----|-----|-----|-----|------|
| Gln | Lys | Ala | Ala | Glu | Ala | Thr | Lys | Val | Ala | Glu | Ala | Glu | Lys | Gln | Lys |      |
|     |     | 515 |     |     |     |     | 520 |     |     |     |     | 525 |     |     |     |      |

| GCA | GCT | GAA | GCC | ACG | AAG | GTT | GCC | GAA | GCG | GAG | AAG | CAG | AAG | GCA | GCT | 1632 |
|-----|-----|-----|-----|-----|-----|-----|-----|-----|-----|-----|-----|-----|-----|-----|-----|------|
| Ala | Ala | Glu | Ala | Thr | Lys | Val | Ala | Glu | Ala | Glu | Lys | Gln | Lys | Ala | Ala |      |
|     | 530 |     |     |     |     | 535 |     |     |     |     | 540 |     |     |     |     |      |

| GAA | GCC | ACG | AAG | GTT | GCC | GAA | GCG | GAG | AAG | CAG | AAG | GCA | GGG | GAA | TTC | 1680 |
|-----|-----|-----|-----|-----|-----|-----|-----|-----|-----|-----|-----|-----|-----|-----|-----|------|
| Glu | Ala | Thr | Lys | Val | Ala | Glu | Ala | Glu | Lys | Gln | Lys | Ala | Gly | Glu | Phe |      |
| 545 |     |     |     |     | 550 |     |     |     |     | 555 |     |     |     |     | 560 |      |

| ATC | GTG | ACT | GAC | TGA | 1695 |
|-----|-----|-----|-----|-----|------|
| Ile | Val | Thr | Asp |     |      |

( 2 ) INFORMATION FOR SEQ ID NO:2:

( i ) SEQUENCE CHARACTERISTICS:
        ( A ) LENGTH: 564 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                 20                  25                  30

Tyr Glu Arg Asp Glu Gly Asp Lys Trp Arg Asn Lys Lys Phe Glu Leu
             35                  40                  45

Gly Leu Glu Phe Pro Asn Leu Pro Tyr Tyr Ile Asp Gly Asp Val Lys
         50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
             115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
             180                 185                 190

Leu Lys Ser Ser Lys Tyr Ile Ala Trp Pro Leu Gln Gly Trp Gln Ala
         195                 200                 205

Thr Phe Gly Gly Gly Asp His Pro Pro Lys Ser Asp Leu Val Pro Arg
    210                 215                 220

Gly Ser Pro Ser Gln Leu Gln Gln Ala Glu Asn Asn Ile Thr Asn Ser
225                 230                 235                 240

Lys Lys Glu Met Thr Lys Leu Arg Glu Lys Val Lys Lys Ala Glu Lys
                245                 250                 255

Glu Lys Leu Asp Ala Ile Asn Arg Ala Thr Lys Leu Glu Glu Glu Arg
             260                 265                 270

Asn Gln Ala Tyr Lys Ala Ala His Lys Ala Glu Glu Lys Ala Lys
         275                 280                 285

Thr Phe Gln Arg Leu Ile Thr Phe Glu Ser Glu Asn Ile Asn Leu Lys
    290                 295                 300

Lys Arg Pro Asn Asp Ala Val Ser Asn Arg Asp Lys Lys Lys Asn Ser
305                 310                 315                 320

Glu Thr Ala Lys Thr Asp Glu Val Glu Lys Gln Arg Ala Ala Glu Ala
                325                 330                 335

Ala Lys Ala Val Glu Thr Glu Lys Gln Arg Ala Ala Glu Ala Thr Lys
         340                 345                 350

Val Ala Glu Ala Glu Lys Arg Lys Ala Ala Glu Ala Ala Lys Ala Val
    355                 360                 365

Glu Thr Glu Lys Gln Arg Ala Ala Glu Ala Thr Lys Val Ala Glu Ala
    370                 375                 380

Glu Lys Gln Lys Ala Ala Glu Ala Ala Lys Ala Val Glu Thr Glu Lys
385                 390                 395                 400
```

| | | | | | | | | | | | | | | |
|---|---|---|---|---|---|---|---|---|---|---|---|---|---|---|
| Gln | Arg | Ala | Ala | Glu | Ala | Thr | Lys | Val | Ala | Glu | Ala | Glu | Lys | Gln | Arg |
| | | | | 405 | | | | | 410 | | | | | 415 | |
| Ala | Ala | Glu | Ala | Met | Lys | Val | Ala | Glu | Ala | Glu | Lys | Gln | Lys | Ala | Ala |
| | | | 420 | | | | | 425 | | | | | 430 | | |
| Glu | Ala | Thr | Lys | Val | Ala | Glu | Ala | Glu | Lys | Gln | Lys | Ala | Ala | Glu | Ala |
| | | | 435 | | | | | 440 | | | | | 445 | | |
| Thr | Lys | Val | Ala | Glu | Ala | Glu | Lys | Gln | Lys | Ala | Ala | Glu | Ala | Thr | Lys |
| | | 450 | | | | | | 455 | | | | | 460 | | |
| Val | Ala | Glu | Ala | Glu | Lys | Gln | Lys | Ala | Ala | Glu | Ala | Thr | Lys | Val | Ala |
| 465 | | | | | 470 | | | | | 475 | | | | | 480 |
| Glu | Ala | Glu | Lys | Gln | Lys | Ala | Ala | Glu | Ala | Thr | Lys | Val | Ala | Glu | Ala |
| | | | | 485 | | | | | 490 | | | | | 495 | |
| Glu | Lys | Gln | Lys | Ala | Ala | Glu | Ala | Thr | Lys | Val | Ala | Glu | Ala | Glu | Lys |
| | | | 500 | | | | | 505 | | | | | 510 | | |
| Gln | Lys | Ala | Ala | Glu | Ala | Thr | Lys | Val | Ala | Glu | Ala | Glu | Lys | Gln | Lys |
| | | | 515 | | | | | 520 | | | | | 525 | | |
| Ala | Ala | Glu | Ala | Thr | Lys | Val | Ala | Glu | Ala | Glu | Lys | Gln | Lys | Ala | Ala |
| | | | 530 | | | | | 535 | | | | | 540 | | |
| Glu | Ala | Thr | Lys | Val | Ala | Glu | Ala | Glu | Lys | Gln | Lys | Ala | Gly | Glu | Phe |
| 545 | | | | | 550 | | | | | 555 | | | | | 560 |
| Ile | Val | Thr | Asp | | | | | | | | | | | | |

( 2 ) INFORMATION FOR SEQ ID NO:3:

( i ) SEQUENCE CHARACTERISTICS:
        ( A ) LENGTH: 1065 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1062

( x i ) SEQUENCE DESCRIPTION: SEQ ID NO:3:

| | | | | | | | | | | | | | | | |
|---|---|---|---|---|---|---|---|---|---|---|---|---|---|---|---|
| ATG | TCC | CCT | ATA | CTA | GGT | TAT | TGG | AAA | ATT | AAG | GGC | CTT | GTG | CAA | CCC | 48 |
| Met | Ser | Pro | Ile | Leu | Gly | Tyr | Trp | Lys | Ile | Lys | Gly | Leu | Val | Gln | Pro | |
| 1 | | | | 5 | | | | | 10 | | | | | 15 | | |
| ACT | CGA | CTT | CTT | TTG | GAA | TAT | CTT | GAA | GAA | AAA | TAT | GAA | GAG | CAT | TTG | 96 |
| Thr | Arg | Leu | Leu | Leu | Glu | Tyr | Leu | Glu | Glu | Lys | Tyr | Glu | Glu | His | Leu | |
| | | | | 20 | | | | | 25 | | | | | 30 | | |
| TAT | GAG | CGC | GAT | GAA | GGT | GAT | AAA | TGG | CGA | AAC | AAA | AAG | TTT | GAA | TTG | 144 |
| Tyr | Glu | Arg | Asp | Glu | Gly | Asp | Lys | Trp | Arg | Asn | Lys | Lys | Phe | Glu | Leu | |
| | | 35 | | | | | 40 | | | | | 45 | | | | |
| GGT | TTG | GAG | TTT | CCC | AAT | CTT | CCT | TAT | TAT | ATT | GAT | GGT | GAT | GTT | AAA | 192 |
| Gly | Leu | Glu | Phe | Pro | Asn | Leu | Pro | Tyr | Tyr | Ile | Asp | Gly | Asp | Val | Lys | |
| | | 50 | | | | | 55 | | | | | 60 | | | | |
| TTA | ACA | CAG | TCT | ATG | GCC | ATC | ATA | CGT | TAT | ATA | GCT | GAC | AAG | CAC | AAC | 240 |
| Leu | Thr | Gln | Ser | Met | Ala | Ile | Ile | Arg | Tyr | Ile | Ala | Asp | Lys | His | Asn | |
| 65 | | | | | 70 | | | | | 75 | | | | | 80 | |
| ATG | TTG | GGT | GGT | TGT | CCA | AAA | GAG | CGT | GCA | GAG | ATT | TCA | ATG | CTT | GAA | 288 |
| Met | Leu | Gly | Gly | Cys | Pro | Lys | Glu | Arg | Ala | Glu | Ile | Ser | Met | Leu | Glu | |
| | | | | 85 | | | | | 90 | | | | | 95 | | |
| GGA | GCG | GTT | TTG | GAT | ATT | AGA | TAC | GGT | GTT | TCG | AGA | ATT | GCA | TAT | AGT | 336 |
| Gly | Ala | Val | Leu | Asp | Ile | Arg | Tyr | Gly | Val | Ser | Arg | Ile | Ala | Tyr | Ser | |
| | | | 100 | | | | | 105 | | | | | 110 | | | |
| AAA | GAC | TTT | GAA | ACT | CTC | AAA | GTT | GAT | TTT | CTT | AGC | AAG | CTA | CCT | GAA | 384 |
| Lys | Asp | Phe | Glu | Thr | Leu | Lys | Val | Asp | Phe | Leu | Ser | Lys | Leu | Pro | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| ATG | CTG | AAA | ATG | TTC | GAA | GAT | CGT | TTA | TGT | CAT | AAA | ACA | TAT | TTA | AAT | 432 |
| Met | Leu | Lys | Met | Phe | Glu | Asp | Arg | Leu | Cys | His | Lys | Thr | Tyr | Leu | Asn | |
| | 130 | | | | 135 | | | | | 140 | | | | | | |
| GGT | GAT | CAT | GTA | ACC | CAT | CCT | GAC | TTC | ATG | TTG | TAT | GAC | GCT | CTT | GAT | 480 |
| Gly | Asp | His | Val | Thr | His | Pro | Asp | Phe | Met | Leu | Tyr | Asp | Ala | Leu | Asp | |
| 145 | | | | | 150 | | | | | 155 | | | | | 160 | |
| GTT | GTT | TTA | TAC | ATG | GAC | CCA | ATG | TGC | CTG | GAT | GCG | TTC | CCA | AAA | TTA | 528 |
| Val | Val | Leu | Tyr | Met | Asp | Pro | Met | Cys | Leu | Asp | Ala | Phe | Pro | Lys | Leu | |
| | | | | 165 | | | | | 170 | | | | | 175 | | |
| GTT | TGT | TTT | AAA | AAA | CGT | ATT | GAA | GCT | ATC | CCA | CAA | ATT | GAT | AAG | TAC | 576 |
| Val | Cys | Phe | Lys | Lys | Arg | Ile | Glu | Ala | Ile | Pro | Gln | Ile | Asp | Lys | Tyr | |
| | | | 180 | | | | | 185 | | | | | 190 | | | |
| TTG | AAA | TCC | AGC | AAG | TAT | ATA | GCA | TGG | CCT | TTG | CAG | GGC | TGG | CAA | GCC | 624 |
| Leu | Lys | Ser | Ser | Lys | Tyr | Ile | Ala | Trp | Pro | Leu | Gln | Gly | Trp | Gln | Ala | |
| | | | 195 | | | | | 200 | | | | | 205 | | | |
| ACG | TTT | GGT | GGT | GGC | GAC | CAT | CCT | CCA | AAA | TCG | GAT | CTG | GTT | CCG | CGT | 672 |
| Thr | Phe | Gly | Gly | Gly | Asp | His | Pro | Pro | Lys | Ser | Asp | Leu | Val | Pro | Arg | |
| | 210 | | | | | 215 | | | | | 220 | | | | | |
| GGA | TCC | CCG | TCC | CAG | CTC | CAA | CAG | GCA | GAA | AAT | AAT | ATC | ACT | AAT | TCC | 720 |
| Gly | Ser | Pro | Ser | Gln | Leu | Gln | Gln | Ala | Glu | Asn | Asn | Ile | Thr | Asn | Ser | |
| 225 | | | | | 230 | | | | | 235 | | | | | 240 | |
| AAA | AAA | GAA | ATG | ACA | AAG | CTA | CGA | GAA | AAA | GTG | AAA | AAG | GCC | GAG | AAA | 768 |
| Lys | Lys | Glu | Met | Thr | Lys | Leu | Arg | Glu | Lys | Val | Lys | Lys | Ala | Glu | Lys | |
| | | | | 245 | | | | | 250 | | | | | 255 | | |
| GAA | AAA | TTG | GAC | GCC | ATT | AAC | CGG | GCA | ACC | AAG | CTG | GAA | GAG | GAA | CGA | 816 |
| Glu | Lys | Leu | Asp | Ala | Ile | Asn | Arg | Ala | Thr | Lys | Leu | Glu | Glu | Glu | Arg | |
| | | | 260 | | | | | 265 | | | | | 270 | | | |
| AAC | CAA | GCG | TAC | AAA | GCA | GCA | CAC | AAG | GCA | GAG | GAG | GAA | AAG | GCT | AAA | 864 |
| Asn | Gln | Ala | Tyr | Lys | Ala | Ala | His | Lys | Ala | Glu | Glu | Glu | Lys | Ala | Lys | |
| | | 275 | | | | | 280 | | | | | 285 | | | | |
| ACA | TTT | CAA | CGC | CTT | ATA | ACA | TTT | GAG | TCG | GAA | AAT | ATT | AAC | TTA | AAG | 912 |
| Thr | Phe | Gln | Arg | Leu | Ile | Thr | Phe | Glu | Ser | Glu | Asn | Ile | Asn | Leu | Lys | |
| | 290 | | | | | 295 | | | | | 300 | | | | | |
| AAA | AGG | CCA | AAT | GAC | GCA | GTT | TCA | AAT | CGG | GAT | AAG | AAA | AAA | AAT | TCT | 960 |
| Lys | Arg | Pro | Asn | Asp | Ala | Val | Ser | Asn | Arg | Asp | Lys | Lys | Lys | Asn | Ser | |
| 305 | | | | | 310 | | | | | 315 | | | | | 320 | |
| GAA | ACC | GCA | AAA | ACT | GAC | GAA | GTA | GAG | AAA | CAG | AGG | GCG | GCT | GAG | GCT | 1008 |
| Glu | Thr | Ala | Lys | Thr | Asp | Glu | Val | Glu | Lys | Gln | Arg | Ala | Ala | Glu | Ala | |
| | | | | 325 | | | | | 330 | | | | | 335 | | |
| GCC | AAG | GCC | GTG | GAG | ACG | GAG | AAG | CAG | AGG | GCA | GGG | GAA | TTC | ATC | GTG | 1056 |
| Ala | Lys | Ala | Val | Glu | Thr | Glu | Lys | Gln | Arg | Ala | Gly | Glu | Phe | Ile | Val | |
| | | | 340 | | | | | 345 | | | | | 350 | | | |
| ACT | GAC | TGA | | | | | | | | | | | | | | 1065 |
| Thr | Asp | | | | | | | | | | | | | | | |

( 2 ) INFORMATION FOR SEQ ID NO:4:

( i ) SEQUENCE CHARACTERISTICS:
        ( A ) LENGTH: 354 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ser | Pro | Ile | Leu | Gly | Tyr | Trp | Lys | Ile | Lys | Gly | Leu | Val | Gln | Pro |
| 1 | | | | 5 | | | | | 10 | | | | | 15 | |
| Thr | Arg | Leu | Leu | Leu | Glu | Tyr | Leu | Glu | Glu | Lys | Tyr | Glu | Glu | His | Leu |
| | | | 20 | | | | | 25 | | | | | 30 | | |
| Tyr | Glu | Arg | Asp | Glu | Gly | Asp | Lys | Trp | Arg | Asn | Lys | Lys | Phe | Glu | Leu |
| | | 35 | | | | | 40 | | | | | 45 | | | |

-continued

```
Gly  Leu  Glu  Phe  Pro  Asn  Leu  Pro  Tyr  Tyr  Ile  Asp  Gly  Asp  Val  Lys
          50                      55                      60

Leu  Thr  Gln  Ser  Met  Ala  Ile  Ile  Arg  Tyr  Ile  Ala  Asp  Lys  His  Asn
 65                      70                      75                           80

Met  Leu  Gly  Gly  Cys  Pro  Lys  Glu  Arg  Ala  Glu  Ile  Ser  Met  Leu  Glu
                    85                      90                          95

Gly  Ala  Val  Leu  Asp  Ile  Arg  Tyr  Gly  Val  Ser  Arg  Ile  Ala  Tyr  Ser
               100                     105                     110

Lys  Asp  Phe  Glu  Thr  Leu  Lys  Val  Asp  Phe  Leu  Ser  Lys  Leu  Pro  Glu
          115                     120                     125

Met  Leu  Lys  Met  Phe  Glu  Asp  Arg  Leu  Cys  His  Lys  Thr  Tyr  Leu  Asn
     130                     135                     140

Gly  Asp  His  Val  Thr  His  Pro  Asp  Phe  Met  Leu  Tyr  Asp  Ala  Leu  Asp
145                          150                     155                     160

Val  Val  Leu  Tyr  Met  Asp  Pro  Met  Cys  Leu  Asp  Ala  Phe  Pro  Lys  Leu
                    165                     170                     175

Val  Cys  Phe  Lys  Lys  Arg  Ile  Glu  Ala  Ile  Pro  Gln  Ile  Asp  Lys  Tyr
               180                     185                     190

Leu  Lys  Ser  Ser  Lys  Tyr  Ile  Ala  Trp  Pro  Leu  Gln  Gly  Trp  Gln  Ala
          195                     200                     205

Thr  Phe  Gly  Gly  Gly  Asp  His  Pro  Pro  Lys  Ser  Asp  Leu  Val  Pro  Arg
     210                     215                     220

Gly  Ser  Pro  Ser  Gln  Leu  Gln  Gln  Ala  Glu  Asn  Asn  Ile  Thr  Asn  Ser
225                     230                     235                          240

Lys  Lys  Glu  Met  Thr  Lys  Leu  Arg  Glu  Lys  Val  Lys  Lys  Ala  Glu  Lys
               245                     250                     255

Glu  Lys  Leu  Asp  Ala  Ile  Asn  Arg  Ala  Thr  Lys  Leu  Glu  Glu  Glu  Arg
          260                     265                     270

Asn  Gln  Ala  Tyr  Lys  Ala  Ala  His  Lys  Ala  Glu  Glu  Lys  Ala  Lys
          275                     280                     285

Thr  Phe  Gln  Arg  Leu  Ile  Thr  Phe  Glu  Ser  Glu  Asn  Ile  Asn  Leu  Lys
     290                     295                     300

Lys  Arg  Pro  Asn  Asp  Ala  Val  Ser  Asn  Arg  Asp  Lys  Lys  Lys  Asn  Ser
305                     310                     315                          320

Glu  Thr  Ala  Lys  Thr  Asp  Glu  Val  Glu  Lys  Gln  Arg  Ala  Ala  Glu  Ala
                    325                     330                     335

Ala  Lys  Ala  Val  Glu  Thr  Glu  Lys  Gln  Arg  Ala  Gly  Glu  Phe  Ile  Val
               340                     345                     350

Thr  Asp
```

( 2 ) INFORMATION FOR SEQ ID NO:5:

( i ) SEQUENCE CHARACTERISTICS:
        ( A ) LENGTH: 924 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..921

( x i ) SEQUENCE DESCRIPTION: SEQ ID NO:5:

```
ATG  TCC  CCT  ATA  CTA  GGT  TAT  TGG  AAA  ATT  AAG  GGC  CTT  GTG  CAA  CCC    48
Met  Ser  Pro  Ile  Leu  Gly  Tyr  Trp  Lys  Ile  Lys  Gly  Leu  Val  Gln  Pro
 1                   5                       10                      15
```

| | | | | | | | | | | | | | | | | |
|---|---|---|---|---|---|---|---|---|---|---|---|---|---|---|---|---|
| ACT | CGA | CTT | CTT | TTG | GAA | TAT | CTT | GAA | GAA | AAA | TAT | GAA | GAG | CAT | TTG | 96 |
| Thr | Arg | Leu | Leu | Leu | Glu | Tyr | Leu | Glu | Glu | Lys | Tyr | Glu | Glu | His | Leu | |
| | | | 20 | | | | 25 | | | | | 30 | | | | |
| TAT | GAG | CGC | GAT | GAA | GGT | GAT | AAA | TGG | CGA | AAC | AAA | AAG | TTT | GAA | TTG | 144 |
| Tyr | Glu | Arg | Asp | Glu | Gly | Asp | Lys | Trp | Arg | Asn | Lys | Lys | Phe | Glu | Leu | |
| | | 35 | | | | | 40 | | | | | 45 | | | | |
| GGT | TTG | GAG | TTT | CCC | AAT | CTT | CCT | TAT | TAT | ATT | GAT | GGT | GAT | GTT | AAA | 192 |
| Gly | Leu | Glu | Phe | Pro | Asn | Leu | Pro | Tyr | Tyr | Ile | Asp | Gly | Asp | Val | Lys | |
| | 50 | | | | | 55 | | | | | | 60 | | | | |
| TTA | ACA | CAG | TCT | ATG | GCC | ATC | ATA | CGT | TAT | ATA | GCT | GAC | AAG | CAC | AAC | 240 |
| Leu | Thr | Gln | Ser | Met | Ala | Ile | Ile | Arg | Tyr | Ile | Ala | Asp | Lys | His | Asn | |
| 65 | | | | | 70 | | | | | 75 | | | | | 80 | |
| ATG | TTG | GGT | GGT | TGT | CCA | AAA | GAG | CGT | GCA | GAG | ATT | TCA | ATG | CTT | GAA | 288 |
| Met | Leu | Gly | Gly | Cys | Pro | Lys | Glu | Arg | Ala | Glu | Ile | Ser | Met | Leu | Glu | |
| | | | | 85 | | | | | 90 | | | | | 95 | | |
| GGA | GCG | GTT | TTG | GAT | ATT | AGA | TAC | GGT | GTT | TCG | AGA | ATT | GCA | TAT | AGT | 336 |
| Gly | Ala | Val | Leu | Asp | Ile | Arg | Tyr | Gly | Val | Ser | Arg | Ile | Ala | Tyr | Ser | |
| | | | 100 | | | | | 105 | | | | | 110 | | | |
| AAA | GAC | TTT | GAA | ACT | CTC | AAA | GTT | GAT | TTT | CTT | AGC | AAG | CTA | CCT | GAA | 384 |
| Lys | Asp | Phe | Glu | Thr | Leu | Lys | Val | Asp | Phe | Leu | Ser | Lys | Leu | Pro | Glu | |
| | | 115 | | | | | 120 | | | | | 125 | | | | |
| ATG | CTG | AAA | ATG | TTC | GAA | GAT | CGT | TTA | TGT | CAT | AAA | ACA | TAT | TTA | AAT | 432 |
| Met | Leu | Lys | Met | Phe | Glu | Asp | Arg | Leu | Cys | His | Lys | Thr | Tyr | Leu | Asn | |
| | 130 | | | | | 135 | | | | | 140 | | | | | |
| GGT | GAT | CAT | GTA | ACC | CAT | CCT | GAC | TTC | ATG | TTG | TAT | GAC | GCT | CTT | GAT | 480 |
| Gly | Asp | His | Val | Thr | His | Pro | Asp | Phe | Met | Leu | Tyr | Asp | Ala | Leu | Asp | |
| 145 | | | | | 150 | | | | | 155 | | | | | 160 | |
| GTT | GTT | TTA | TAC | ATG | GAC | CCA | ATG | TGC | CTG | GAT | GCG | TTC | CCA | AAA | TTA | 528 |
| Val | Val | Leu | Tyr | Met | Asp | Pro | Met | Cys | Leu | Asp | Ala | Phe | Pro | Lys | Leu | |
| | | | | 165 | | | | | 170 | | | | | 175 | | |
| GTT | TGT | TTT | AAA | AAA | CGT | ATT | GAA | GCT | ATC | CCA | CAA | ATT | GAT | AAG | TAC | 576 |
| Val | Cys | Phe | Lys | Lys | Arg | Ile | Glu | Ala | Ile | Pro | Gln | Ile | Asp | Lys | Tyr | |
| | | | 180 | | | | | 185 | | | | | 190 | | | |
| TTG | AAA | TCC | AGC | AAG | TAT | ATA | GCA | TGG | CCT | TTG | CAG | GGC | TGG | CAA | GCC | 624 |
| Leu | Lys | Ser | Ser | Lys | Tyr | Ile | Ala | Trp | Pro | Leu | Gln | Gly | Trp | Gln | Ala | |
| | | 195 | | | | | 200 | | | | | 205 | | | | |
| ACG | TTT | GGT | GGT | GGC | GAC | CAT | CCT | CCA | AAA | TCG | GAT | CCC | CCT | GAA | GCT | 672 |
| Thr | Phe | Gly | Gly | Gly | Asp | His | Pro | Pro | Lys | Ser | Asp | Pro | Pro | Glu | Ala | |
| | 210 | | | | | 215 | | | | | 220 | | | | | |
| GCC | AAG | GCT | ATG | GAG | TCG | CAG | AAG | CAG | AGA | TTC | TTA | GAA | CGT | TTT | GCG | 720 |
| Ala | Lys | Ala | Met | Glu | Ser | Gln | Lys | Gln | Arg | Phe | Leu | Glu | Arg | Phe | Ala | |
| 225 | | | | | 230 | | | | | 235 | | | | | 240 | |
| GTT | CTT | GAG | GAG | GAG | AAA | AAG | GCA | GCC | TTA | AGA | GCG | GCG | GAG | ATG | GAG | 768 |
| Val | Leu | Glu | Glu | Glu | Lys | Lys | Ala | Ala | Leu | Arg | Ala | Ala | Glu | Met | Glu | |
| | | | | 245 | | | | | 250 | | | | | 255 | | |
| AGG | AGG | AAA | ATA | ACA | AAC | ATA | ATG | AAG | AAT | AAA | GGT | GTA | CGC | AGT | TCG | 816 |
| Arg | Arg | Lys | Ile | Thr | Asn | Ile | Met | Lys | Asn | Lys | Gly | Val | Arg | Ser | Ser | |
| | | | 260 | | | | | 265 | | | | | 270 | | | |
| GAT | TCG | GTG | CCG | CTT | GTG | GAG | GGG | AAT | CGC | TCT | GTT | ACT | GAG | AGT | TCT | 864 |
| Asp | Ser | Val | Pro | Leu | Val | Glu | Gly | Asn | Arg | Ser | Val | Thr | Glu | Ser | Ser | |
| | | 275 | | | | | 280 | | | | | 285 | | | | |
| TGT | AGA | AAT | CGG | TTT | CGT | TTT | TGT | AGA | AAT | CGG | TTT | CGT | TTT | TCA | TGT | 912 |
| Cys | Arg | Asn | Arg | Phe | Arg | Phe | Cys | Arg | Asn | Arg | Phe | Arg | Phe | Ser | Cys | |
| | 290 | | | | | 295 | | | | | 300 | | | | | |
| TCT | GTA | ATG | TGA | | | | | | | | | | | | | 924 |
| Ser | Val | Met | | | | | | | | | | | | | | |
| 305 | | | | | | | | | | | | | | | | |

( 2 ) INFORMATION FOR SEQ ID NO:6:

(i) SEQUENCE CHARACTERISTICS:
   (A) LENGTH: 307 amino acids
   (B) TYPE: amino acid
   (D) TOPOLOGY: linear (ii) MOLECULE TYPE: protein (xi) SEQUENCE DESCRIPTION: SEQ ID NO:6:

| Met | Ser | Pro | Ile | Leu | Gly | Tyr | Trp | Lys | Ile | Lys | Gly | Leu | Val | Gln | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Arg | Leu | Leu | Leu | Glu | Tyr | Leu | Glu | Glu | Lys | Tyr | Glu | Glu | His | Leu |
|     |     |     |     | 20  |     |     |     |     | 25  |     |     |     |     | 30  |     |
| Tyr | Glu | Arg | Asp | Glu | Gly | Asp | Lys | Trp | Arg | Asn | Lys | Lys | Phe | Glu | Leu |
|     |     |     | 35  |     |     |     |     | 40  |     |     |     |     | 45  |     |     |
| Gly | Leu | Glu | Phe | Pro | Asn | Leu | Pro | Tyr | Tyr | Ile | Asp | Gly | Asp | Val | Lys |
|     |     | 50  |     |     |     |     | 55  |     |     |     |     |     | 60  |     |     |
| Leu | Thr | Gln | Ser | Met | Ala | Ile | Ile | Arg | Tyr | Ile | Ala | Asp | Lys | His | Asn |
| 65  |     |     |     |     | 70  |     |     |     |     | 75  |     |     |     |     | 80  |
| Met | Leu | Gly | Gly | Cys | Pro | Lys | Glu | Arg | Ala | Glu | Ile | Ser | Met | Leu | Glu |
|     |     |     |     | 85  |     |     |     |     | 90  |     |     |     |     | 95  |     |
| Gly | Ala | Val | Leu | Asp | Ile | Arg | Tyr | Gly | Val | Ser | Arg | Ile | Ala | Tyr | Ser |
|     |     |     | 100 |     |     |     |     | 105 |     |     |     |     | 110 |     |     |
| Lys | Asp | Phe | Glu | Thr | Leu | Lys | Val | Asp | Phe | Leu | Ser | Lys | Leu | Pro | Glu |
|     |     | 115 |     |     |     |     | 120 |     |     |     |     | 125 |     |     |     |
| Met | Leu | Lys | Met | Phe | Glu | Asp | Arg | Leu | Cys | His | Lys | Thr | Tyr | Leu | Asn |
|     | 130 |     |     |     |     | 135 |     |     |     |     | 140 |     |     |     |     |
| Gly | Asp | His | Val | Thr | His | Pro | Asp | Phe | Met | Leu | Tyr | Asp | Ala | Leu | Asp |
| 145 |     |     |     |     | 150 |     |     |     |     | 155 |     |     |     |     | 160 |
| Val | Val | Leu | Tyr | Met | Asp | Pro | Met | Cys | Leu | Asp | Ala | Phe | Pro | Lys | Leu |
|     |     |     |     | 165 |     |     |     |     | 170 |     |     |     |     | 175 |     |
| Val | Cys | Phe | Lys | Lys | Arg | Ile | Glu | Ala | Ile | Pro | Gln | Ile | Asp | Lys | Tyr |
|     |     |     | 180 |     |     |     |     | 185 |     |     |     |     | 190 |     |     |
| Leu | Lys | Ser | Ser | Lys | Tyr | Ile | Ala | Trp | Pro | Leu | Gln | Gly | Trp | Gln | Ala |
|     |     | 195 |     |     |     |     | 200 |     |     |     |     | 205 |     |     |     |
| Thr | Phe | Gly | Gly | Gly | Asp | His | Pro | Pro | Lys | Ser | Asp | Pro | Pro | Glu | Ala |
|     | 210 |     |     |     |     | 215 |     |     |     |     | 220 |     |     |     |     |
| Ala | Lys | Ala | Met | Glu | Ser | Gln | Lys | Gln | Arg | Phe | Leu | Glu | Arg | Phe | Ala |
| 225 |     |     |     |     | 230 |     |     |     |     | 235 |     |     |     |     | 240 |
| Val | Leu | Glu | Glu | Glu | Lys | Lys | Ala | Ala | Leu | Arg | Ala | Ala | Glu | Met | Glu |
|     |     |     |     | 245 |     |     |     |     | 250 |     |     |     |     | 255 |     |
| Arg | Arg | Lys | Ile | Thr | Asn | Ile | Met | Lys | Asn | Lys | Gly | Val | Arg | Ser | Ser |
|     |     |     | 260 |     |     |     |     | 265 |     |     |     |     | 270 |     |     |
| Asp | Ser | Val | Pro | Leu | Val | Glu | Gly | Asn | Arg | Ser | Val | Thr | Glu | Ser | Ser |
|     |     | 275 |     |     |     |     | 280 |     |     |     |     | 285 |     |     |     |
| Cys | Arg | Asn | Arg | Phe | Arg | Phe | Cys | Arg | Asn | Arg | Phe | Arg | Phe | Ser | Cys |
|     | 290 |     |     |     |     | 295 |     |     |     |     | 300 |     |     |     |     |
| Ser | Val | Met |
| 305 |     |     |

(2) INFORMATION FOR SEQ ID NO:7:

(i) SEQUENCE CHARACTERISTICS:
      (A) LENGTH: 1932 base pairs
      (B) TYPE: nucleic acid
      (C) STRANDEDNESS: double
      (D) TOPOLOGY: linear (ii) MOLECULE TYPE: DNA (genomic)

( i x ) FEATURE:
    ( A ) NAME/KEY: CDS
    ( B ) LOCATION: 1..1929

( x i ) SEQUENCE DESCRIPTION: SEQ ID NO:7:

```
ATG TCC CCT ATA CTA GGT TAT TGG AAA ATT AAG GGC CTT GTG CAA CCC      48
Met Ser Pro Ile Leu Gly Tyr Trp Lys Ile Lys Gly Leu Val Gln Pro
 1           5                  10                  15

ACT CGA CTT CTT TTG GAA TAT CTT GAA GAA AAA TAT GAA GAG CAT TTG      96
Thr Arg Leu Leu Leu Glu Tyr Leu Glu Glu Lys Tyr Glu Glu His Leu
             20                  25                  30

TAT GAG CGC GAT GAA GGT GAT AAA TGG CGA AAC AAA AAG TTT GAA TTG     144
Tyr Glu Arg Asp Glu Gly Asp Lys Trp Arg Asn Lys Lys Phe Glu Leu
         35                  40                  45

GGT TTG GAG TTT CCC AAT CTT CCT TAT TAT ATT GAT GGT GAT GTT AAA     192
Gly Leu Glu Phe Pro Asn Leu Pro Tyr Tyr Ile Asp Gly Asp Val Lys
 50                  55                  60

TTA ACA CAG TCT ATG GCC ATC ATA CGT TAT ATA GCT GAC AAG CAC AAC     240
Leu Thr Gln Ser Met Ala Ile Ile Arg Tyr Ile Ala Asp Lys His Asn
 65                  70                  75                  80

ATG TTG GGT GGT TGT CCA AAA GAG CGT GCA GAG ATT TCA ATG CTT GAA     288
Met Leu Gly Gly Cys Pro Lys Glu Arg Ala Glu Ile Ser Met Leu Glu
                 85                  90                  95

GGA GCG GTT TTG GAT ATT AGA TAC GGT GTT TCG AGA ATT GCA TAT AGT     336
Gly Ala Val Leu Asp Ile Arg Tyr Gly Val Ser Arg Ile Ala Tyr Ser
             100                 105                 110

AAA GAC TTT GAA ACT CTC AAA GTT GAT TTT CTT AGC AAG CTA CCT GAA     384
Lys Asp Phe Glu Thr Leu Lys Val Asp Phe Leu Ser Lys Leu Pro Glu
         115                 120                 125

ATG CTG AAA ATG TTC GAA GAT CGT TTA TGT CAT AAA ACA TAT TTA AAT     432
Met Leu Lys Met Phe Glu Asp Arg Leu Cys His Lys Thr Tyr Leu Asn
 130                 135                 140

GGT GAT CAT GTA ACC CAT CCT GAC TTC ATG TTG TAT GAC GCT CTT GAT     480
Gly Asp His Val Thr His Pro Asp Phe Met Leu Tyr Asp Ala Leu Asp
 145                 150                 155                 160

GTT GTT TTA TAC ATG GAC CCA ATG TGC CTG GAT GCG TTC CCA AAA TTA     528
Val Val Leu Tyr Met Asp Pro Met Cys Leu Asp Ala Phe Pro Lys Leu
                 165                 170                 175

GTT TGT TTT AAA AAA CGT ATT GAA GCT ATC CCA CAA ATT GAT AAG TAC     576
Val Cys Phe Lys Lys Arg Ile Glu Ala Ile Pro Gln Ile Asp Lys Tyr
             180                 185                 190

TTG AAA TCC AGC AAG TAT ATA GCA TGG CCT TTG CAG GGC TGG CAA GCC     624
Leu Lys Ser Ser Lys Tyr Ile Ala Trp Pro Leu Gln Gly Trp Gln Ala
         195                 200                 205

ACG TTT GGT GGT GGC GAC CAT CCT CCA AAA TCG GAT CTG GTT CCG CGT     672
Thr Phe Gly Gly Gly Asp His Pro Pro Lys Ser Asp Leu Val Pro Arg
 210                 215                 220

GGA TCC CCG TCC CAG CTC CAA CAG GCA GAA AAT AAT ATC ACT AAT TCC     720
Gly Ser Pro Ser Gln Leu Gln Gln Ala Glu Asn Asn Ile Thr Asn Ser
 225                 230                 235                 240

AAA AAA GAA ATG ACA AAG CTA CGA GAA AAA GTG AAA AAG GCC GAG AAA     768
Lys Lys Glu Met Thr Lys Leu Arg Glu Lys Val Lys Lys Ala Glu Lys
                 245                 250                 255

GAA AAA TTG GAC GCC ATT AAC CGG GCA ACC AAG CTG GAA GAG GAA CGA     816
Glu Lys Leu Asp Ala Ile Asn Arg Ala Thr Lys Leu Glu Glu Glu Arg
             260                 265                 270

AAC CAA GCG TAC AAA GCA GCA CAC AAG GCA GAG GAG GAA AAG GCT AAA     864
Asn Gln Ala Tyr Lys Ala Ala His Lys Ala Glu Glu Glu Lys Ala Lys
         275                 280                 285

ACA TTT CAA CGC CTT ATA ACA TTT GAG TCG GAA AAT ATT AAC TTA AAG     912
Thr Phe Gln Arg Leu Ile Thr Phe Glu Ser Glu Asn Ile Asn Leu Lys
```

|     |     |     |     |     | 290 |     |     |     |     | 295 |     |     |     |     | 300 |     |      |
|-----|-----|-----|-----|-----|-----|-----|-----|-----|-----|-----|-----|-----|-----|-----|-----|-----|------|
| AAA | AGG | CCA | AAT | GAC | GCA | GTT | TCA | AAT | CGG | GAT | AAG | AAA | AAA | AAT | TCT |     | 960  |
| Lys | Arg | Pro | Asn | Asp | Ala | Val | Ser | Asn | Arg | Asp | Lys | Lys | Lys | Asn | Ser |     |      |
| 305 |     |     |     |     | 310 |     |     |     |     | 315 |     |     |     |     | 320 |     |      |
| GAA | ACC | GCA | AAA | ACT | GAC | GAA | GTA | GAG | AAA | CAG | AGG | GCG | GCT | GAG | GCT |     | 1008 |
| Glu | Thr | Ala | Lys | Thr | Asp | Glu | Val | Glu | Lys | Gln | Arg | Ala | Ala | Glu | Ala |     |      |
|     |     |     |     | 325 |     |     |     |     | 330 |     |     |     |     | 335 |     |     |      |
| GCC | AAG | GCC | GTG | GAG | ACG | GAG | AAG | CAG | AGG | GCA | GCT | GAG | GCC | ACG | AAG |     | 1056 |
| Ala | Lys | Ala | Val | Glu | Thr | Glu | Lys | Gln | Arg | Ala | Ala | Glu | Ala | Thr | Lys |     |      |
|     |     |     | 340 |     |     |     |     | 345 |     |     |     |     | 350 |     |     |     |      |
| GTT | GCC | GAA | GCG | GAG | AAG | CGG | AAG | GCA | GCT | GAG | GCC | GCC | AAG | GCC | GTG |     | 1104 |
| Val | Ala | Glu | Ala | Glu | Lys | Arg | Lys | Ala | Ala | Glu | Ala | Ala | Lys | Ala | Val |     |      |
|     |     | 355 |     |     |     |     | 360 |     |     |     |     | 365 |     |     |     |     |      |
| GAG | ACG | GAG | AAG | CAG | AGG | GCA | GCT | GAA | GCC | ACG | AAG | GTT | GCC | GAA | GCG |     | 1152 |
| Glu | Thr | Glu | Lys | Gln | Arg | Ala | Ala | Glu | Ala | Thr | Lys | Val | Ala | Glu | Ala |     |      |
| 370 |     |     |     |     | 375 |     |     |     |     | 380 |     |     |     |     |     |     |      |
| GAG | AAG | CAG | AAG | GCA | GCT | GAG | GCC | GCC | AAG | GCC | GTG | GAG | ACG | GAG | AAG |     | 1200 |
| Glu | Lys | Gln | Lys | Ala | Ala | Glu | Ala | Ala | Lys | Ala | Val | Glu | Thr | Glu | Lys |     |      |
| 385 |     |     |     |     | 390 |     |     |     |     | 395 |     |     |     |     | 400 |     |      |
| CAG | AGG | GCA | GCT | GAA | GCC | ACG | AAG | GTT | GCC | GAA | GCG | GAG | AAG | CAG | AGG |     | 1248 |
| Gln | Arg | Ala | Ala | Glu | Ala | Thr | Lys | Val | Ala | Glu | Ala | Glu | Lys | Gln | Arg |     |      |
|     |     |     |     | 405 |     |     |     |     | 410 |     |     |     |     | 415 |     |     |      |
| GCA | GCT | GAA | GCC | ATG | AAG | GTT | GCC | GAA | GCG | GAG | AAG | CAG | AAG | GCA | GCT |     | 1296 |
| Ala | Ala | Glu | Ala | Met | Lys | Val | Ala | Glu | Ala | Glu | Lys | Gln | Lys | Ala | Ala |     |      |
|     |     |     |     | 420 |     |     |     |     | 425 |     |     |     |     | 430 |     |     |      |
| GAG | GCC | ACG | AAG | GTT | GCC | GAA | GCG | GAG | AAG | CAG | AAG | GCA | GCT | GAA | GCC |     | 1344 |
| Glu | Ala | Thr | Lys | Val | Ala | Glu | Ala | Glu | Lys | Gln | Lys | Ala | Ala | Glu | Ala |     |      |
|     |     | 435 |     |     |     |     | 440 |     |     |     |     | 445 |     |     |     |     |      |
| ACG | AAG | GTT | GCC | GAA | GCG | GAG | AAG | CAG | AAG | GCA | GCT | GAA | GCC | ACG | AAG |     | 1392 |
| Thr | Lys | Val | Ala | Glu | Ala | Glu | Lys | Gln | Lys | Ala | Ala | Glu | Ala | Thr | Lys |     |      |
|     | 450 |     |     |     |     | 455 |     |     |     |     | 460 |     |     |     |     |     |      |
| GTT | GCC | GAA | GCG | GAG | AAG | CAG | AAG | GCA | GCT | GAA | GCC | ACG | AAG | GTT | GCC |     | 1440 |
| Val | Ala | Glu | Ala | Glu | Lys | Gln | Lys | Ala | Ala | Glu | Ala | Thr | Lys | Val | Ala |     |      |
| 465 |     |     |     |     | 470 |     |     |     |     | 475 |     |     |     |     | 480 |     |      |
| GAA | GCG | GAG | AAG | CAG | AAG | GCA | GCT | GAA | GCC | ACG | AAG | GTT | GCC | GAA | GCG |     | 1488 |
| Glu | Ala | Glu | Lys | Gln | Lys | Ala | Ala | Glu | Ala | Thr | Lys | Val | Ala | Glu | Ala |     |      |
|     |     |     |     | 485 |     |     |     |     | 490 |     |     |     |     | 495 |     |     |      |
| GAG | AAG | CAG | AAG | GCA | GCT | GAA | GCC | ACG | AAG | GTT | GCC | GAA | GCG | GAG | AAG |     | 1536 |
| Glu | Lys | Gln | Lys | Ala | Ala | Glu | Ala | Thr | Lys | Val | Ala | Glu | Ala | Glu | Lys |     |      |
|     |     |     | 500 |     |     |     |     | 505 |     |     |     |     | 510 |     |     |     |      |
| CAG | AAG | GCA | GCT | GAA | GCC | ACG | AAG | GTT | GCC | GAA | GCG | GAG | AAG | CAG | AAG |     | 1584 |
| Gln | Lys | Ala | Ala | Glu | Ala | Thr | Lys | Val | Ala | Glu | Ala | Glu | Lys | Gln | Lys |     |      |
|     |     | 515 |     |     |     |     | 520 |     |     |     |     | 525 |     |     |     |     |      |
| GCA | GCT | GAA | GCC | ACG | AAG | GTT | GCC | GAA | GCG | GAG | AAG | CAG | AAG | GCA | GCT |     | 1632 |
| Ala | Ala | Glu | Ala | Thr | Lys | Val | Ala | Glu | Ala | Glu | Lys | Gln | Lys | Ala | Ala |     |      |
|     |     | 530 |     |     |     |     | 535 |     |     |     |     | 540 |     |     |     |     |      |
| GAA | GCC | ACG | AAG | GTT | GCC | GAA | GCG | GAG | AAG | CAG | AAG | GCA | GCT | GAA | GCT |     | 1680 |
| Glu | Ala | Thr | Lys | Val | Ala | Glu | Ala | Glu | Lys | Gln | Lys | Ala | Ala | Glu | Ala |     |      |
| 545 |     |     |     |     | 550 |     |     |     |     | 555 |     |     |     |     | 560 |     |      |
| GCC | AAG | GCT | ATG | GAG | TCG | CAG | AAG | CAG | AGA | TTC | TTA | GAA | CGT | TTT | GCG |     | 1728 |
| Ala | Lys | Ala | Met | Glu | Ser | Gln | Lys | Gln | Arg | Phe | Leu | Glu | Arg | Phe | Ala |     |      |
|     |     |     |     | 565 |     |     |     |     | 570 |     |     |     |     | 575 |     |     |      |
| GTT | CTT | GAG | GAG | GAG | AAA | AAG | GCA | GCC | TTA | AGA | GCG | GCG | GAG | ATG | GAG |     | 1776 |
| Val | Leu | Glu | Glu | Glu | Lys | Lys | Ala | Ala | Leu | Arg | Ala | Ala | Glu | Met | Glu |     |      |
|     |     |     | 580 |     |     |     |     | 585 |     |     |     |     | 590 |     |     |     |      |
| AGG | AGG | AAA | ATA | ACA | AAC | ATA | ATG | AAG | AAT | AAA | GGT | GTA | CGC | AGT | TCG |     | 1824 |
| Arg | Arg | Lys | Ile | Thr | Asn | Ile | Met | Lys | Asn | Lys | Gly | Val | Arg | Ser | Ser |     |      |
|     |     | 595 |     |     |     |     | 600 |     |     |     |     | 605 |     |     |     |     |      |
| GAT | TCG | GTG | CCG | CTT | GTG | GAG | GGG | AAT | CGC | TCT | GTT | ACT | GAG | AGT | TCT |     | 1872 |
| Asp | Ser | Val | Pro | Leu | Val | Glu | Gly | Asn | Arg | Ser | Val | Thr | Glu | Ser | Ser |     |      |

```
             610                      615                      620
TGT  AGA  AAT  CGG  TTT  CGT  TTT  TGT  AGA  AAT  CGG  TTT  CGT  TTT  TCA  TGT         1920
Cys  Arg  Asn  Arg  Phe  Arg  Phe  Cys  Arg  Asn  Arg  Phe  Arg  Phe  Ser  Cys
625                      630                      635                      640

TCT  GTA  ATG  TGA                                                                      1932
Ser  Val  Met
```

( 2 ) INFORMATION FOR SEQ ID NO:8:

( i ) SEQUENCE CHARACTERISTICS:
        ( A ) LENGTH: 643 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Ser  Pro  Ile  Leu  Gly  Tyr  Trp  Lys  Ile  Lys  Gly  Leu  Val  Gln  Pro
  1              5                       10                      15

Thr  Arg  Leu  Leu  Leu  Glu  Tyr  Leu  Glu  Glu  Lys  Tyr  Glu  Glu  His  Leu
                20                       25                      30

Tyr  Glu  Arg  Asp  Glu  Gly  Asp  Lys  Trp  Arg  Asn  Lys  Lys  Phe  Glu  Leu
           35                      40                           45

Gly  Leu  Glu  Phe  Pro  Asn  Leu  Pro  Tyr  Tyr  Ile  Asp  Gly  Asp  Val  Lys
      50                      55                      60

Leu  Thr  Gln  Ser  Met  Ala  Ile  Ile  Arg  Tyr  Ile  Ala  Asp  Lys  His  Asn
 65                      70                      75                           80

Met  Leu  Gly  Gly  Cys  Pro  Lys  Glu  Arg  Ala  Glu  Ile  Ser  Met  Leu  Glu
                     85                      90                      95

Gly  Ala  Val  Leu  Asp  Ile  Arg  Tyr  Gly  Val  Ser  Arg  Ile  Ala  Tyr  Ser
                100                      105                     110

Lys  Asp  Phe  Glu  Thr  Leu  Lys  Val  Asp  Phe  Leu  Ser  Lys  Leu  Pro  Glu
          115                      120                     125

Met  Leu  Lys  Met  Phe  Glu  Asp  Arg  Leu  Cys  His  Lys  Thr  Tyr  Leu  Asn
     130                     135                     140

Gly  Asp  His  Val  Thr  His  Pro  Asp  Phe  Met  Leu  Tyr  Asp  Ala  Leu  Asp
145                      150                     155                          160

Val  Val  Leu  Tyr  Met  Asp  Pro  Met  Cys  Leu  Asp  Ala  Phe  Pro  Lys  Leu
                    165                      170                     175

Val  Cys  Phe  Lys  Lys  Arg  Ile  Glu  Ala  Ile  Pro  Gln  Ile  Asp  Lys  Tyr
               180                      185                     190

Leu  Lys  Ser  Ser  Lys  Tyr  Ile  Ala  Trp  Pro  Leu  Gln  Gly  Trp  Gln  Ala
               195                      200                     205

Thr  Phe  Gly  Gly  Gly  Asp  His  Pro  Pro  Lys  Ser  Asp  Leu  Val  Pro  Arg
     210                      215                     220

Gly  Ser  Pro  Ser  Gln  Leu  Gln  Gln  Ala  Glu  Asn  Asn  Ile  Thr  Asn  Ser
225                      230                     235                          240

Lys  Lys  Glu  Met  Thr  Lys  Leu  Arg  Glu  Lys  Val  Lys  Lys  Ala  Glu  Lys
                    245                      250                     255

Glu  Lys  Leu  Asp  Ala  Ile  Asn  Arg  Ala  Thr  Lys  Leu  Glu  Glu  Glu  Arg
               260                      265                     270

Asn  Gln  Ala  Tyr  Lys  Ala  Ala  His  Lys  Ala  Glu  Glu  Lys  Ala  Lys
               275                      280                     285

Thr  Phe  Gln  Arg  Leu  Ile  Thr  Phe  Glu  Ser  Glu  Asn  Ile  Asn  Leu  Lys
     290                      295                     300

Lys  Arg  Pro  Asn  Asp  Ala  Val  Ser  Asn  Arg  Asp  Lys  Lys  Lys  Asn  Ser
305                      310                     315                          320
```

| | | | | | | | | | | | | | | |
|---|---|---|---|---|---|---|---|---|---|---|---|---|---|---|
| Glu | Thr | Ala | Lys | Thr<br>325 | Asp | Glu | Val | Glu | Lys<br>330 | Gln | Arg | Ala | Ala | Glu Ala<br>335 |
| Ala | Lys | Ala | Val<br>340 | Glu | Thr | Glu | Lys<br>345 | Gln | Arg | Ala | Ala | Glu<br>350 | Ala | Thr Lys |
| Val | Ala<br>355 | Glu | Ala | Glu | Lys | Arg<br>360 | Lys | Ala | Ala | Glu | Ala<br>365 | Ala | Lys | Ala Val |
| Glu | Thr<br>370 | Glu | Lys | Gln | Arg | Ala<br>375 | Ala | Glu | Ala | Thr | Lys<br>380 | Val | Ala | Glu Ala |
| Glu<br>385 | Lys | Gln | Lys | Ala | Ala<br>390 | Glu | Ala | Ala | Lys | Ala<br>395 | Val | Glu | Thr | Glu Lys<br>400 |
| Gln | Arg | Ala | Ala | Glu<br>405 | Ala | Thr | Lys | Val | Ala<br>410 | Glu | Ala | Glu | Lys | Gln Arg<br>415 |
| Ala | Ala | Glu | Ala<br>420 | Met | Lys | Val | Ala | Glu<br>425 | Ala | Glu | Lys | Gln | Lys<br>430 | Ala Ala |
| Glu | Ala | Thr<br>435 | Lys | Val | Ala | Glu | Ala<br>440 | Glu | Lys | Gln | Lys | Ala<br>445 | Ala | Glu Ala |
| Thr | Lys<br>450 | Val | Ala | Glu | Ala | Glu<br>455 | Lys | Gln | Lys | Ala | Ala<br>460 | Glu | Ala | Thr Lys |
| Val<br>465 | Ala | Glu | Ala | Glu | Lys<br>470 | Gln | Lys | Ala | Ala | Glu<br>475 | Ala | Thr | Lys | Val Ala<br>480 |
| Glu | Ala | Glu | Lys | Gln<br>485 | Lys | Ala | Ala | Glu | Ala<br>490 | Thr | Lys | Val | Ala | Glu Ala<br>495 |
| Glu | Lys | Gln | Lys<br>500 | Ala | Ala | Glu | Ala | Thr<br>505 | Lys | Val | Ala | Glu | Ala<br>510 | Glu Lys |
| Gln | Lys | Ala<br>515 | Ala | Glu | Ala | Thr | Lys<br>520 | Val | Ala | Glu | Ala | Glu<br>525 | Lys | Gln Lys |
| Ala | Ala<br>530 | Glu | Ala | Thr | Lys | Val<br>535 | Ala | Glu | Ala | Glu | Lys<br>540 | Gln | Lys | Ala Ala |
| Glu<br>545 | Ala | Thr | Lys | Val | Ala<br>550 | Glu | Ala | Glu | Lys | Gln<br>555 | Lys | Ala | Ala | Glu Ala<br>560 |
| Ala | Lys | Ala | Met | Glu<br>565 | Ser | Gln | Lys | Gln | Arg<br>570 | Phe | Leu | Glu | Arg | Phe Ala<br>575 |
| Val | Leu | Glu | Glu<br>580 | Glu | Lys | Lys | Ala | Ala<br>585 | Leu | Arg | Ala | Ala | Glu<br>590 | Met Glu |
| Arg | Arg | Lys<br>595 | Ile | Thr | Asn | Ile | Met<br>600 | Lys | Asn | Lys | Gly | Val<br>605 | Arg | Ser Ser |
| Asp | Ser<br>610 | Val | Pro | Leu | Val | Glu<br>615 | Gly | Asn | Arg | Ser | Val<br>620 | Thr | Glu | Ser Ser |
| Cys<br>625 | Arg | Asn | Arg | Phe | Arg<br>630 | Phe | Cys | Arg | Asn | Arg<br>635 | Phe | Arg | Phe | Ser Cys<br>640 |
| Ser | Val | Met | | | | | | | | | | | | |

( 2 ) INFORMATION FOR SEQ ID NO:9:

( i ) SEQUENCE CHARACTERISTICS:
        ( A ) LENGTH: 1419 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1416

( x i ) SEQUENCE DESCRIPTION: SEQ ID NO:9:

```
ATG  TCC  CCT  ATA  CTA  GGT  TAT  TGG  AAA  ATT  AAG  GGC  CTT  GTG  CAA  CCC     48
Met  Ser  Pro  Ile  Leu  Gly  Tyr  Trp  Lys  Ile  Lys  Gly  Leu  Val  Gln  Pro
 1              5                        10                        15

ACT  CGA  CTT  CTT  TTG  GAA  TAT  CTT  GAA  GAA  AAA  TAT  GAA  GAG  CAT  TTG     96
Thr  Arg  Leu  Leu  Leu  Glu  Tyr  Leu  Glu  Glu  Lys  Tyr  Glu  Glu  His  Leu
                    20                        25                        30

TAT  GAG  CGC  GAT  GAA  GGT  GAT  AAA  TGG  CGA  AAC  AAA  AAG  TTT  GAA  TTG    144
Tyr  Glu  Arg  Asp  Glu  Gly  Asp  Lys  Trp  Arg  Asn  Lys  Lys  Phe  Glu  Leu
               35                        40                        45

GGT  TTG  GAG  TTT  CCC  AAT  CTT  CCT  TAT  TAT  ATT  GAT  GGT  GAT  GTT  AAA    192
Gly  Leu  Glu  Phe  Pro  Asn  Leu  Pro  Tyr  Tyr  Ile  Asp  Gly  Asp  Val  Lys
          50                        55                        60

TTA  ACA  CAG  TCT  ATG  GCC  ATC  ATA  CGT  TAT  ATA  GCT  GAC  AAG  CAC  AAC    240
Leu  Thr  Gln  Ser  Met  Ala  Ile  Ile  Arg  Tyr  Ile  Ala  Asp  Lys  His  Asn
 65                       70                        75                        80

ATG  TTG  GGT  GGT  TGT  CCA  AAA  GAG  CGT  GCA  GAG  ATT  TCA  ATG  CTT  GAA    288
Met  Leu  Gly  Gly  Cys  Pro  Lys  Glu  Arg  Ala  Glu  Ile  Ser  Met  Leu  Glu
                    85                        90                        95

GGA  GCG  GTT  TTG  GAT  ATT  AGA  TAC  GGT  GTT  TCG  AGA  ATT  GCA  TAT  AGT    336
Gly  Ala  Val  Leu  Asp  Ile  Arg  Tyr  Gly  Val  Ser  Arg  Ile  Ala  Tyr  Ser
               100                       105                       110

AAA  GAC  TTT  GAA  ACT  CTC  AAA  GTT  GAT  TTT  CTT  AGC  AAG  CTA  CCT  GAA    384
Lys  Asp  Phe  Glu  Thr  Leu  Lys  Val  Asp  Phe  Leu  Ser  Lys  Leu  Pro  Glu
          115                       120                       125

ATG  CTG  AAA  ATG  TTC  GAA  GAT  CGT  TTA  TGT  CAT  AAA  ACA  TAT  TTA  AAT    432
Met  Leu  Lys  Met  Phe  Glu  Asp  Arg  Leu  Cys  His  Lys  Thr  Tyr  Leu  Asn
     130                       135                       140

GGT  GAT  CAT  GTA  ACC  CAT  CCT  GAC  TTC  ATG  TTG  TAT  GAC  GCT  CTT  GAT    480
Gly  Asp  His  Val  Thr  His  Pro  Asp  Phe  Met  Leu  Tyr  Asp  Ala  Leu  Asp
145                      150                       155                       160

GTT  GTT  TTA  TAC  ATG  GAC  CCA  ATG  TGC  CTG  GAT  GCG  TTC  CCA  AAA  TTA    528
Val  Val  Leu  Tyr  Met  Asp  Pro  Met  Cys  Leu  Asp  Ala  Phe  Pro  Lys  Leu
                    165                       170                       175

GTT  TGT  TTT  AAA  AAA  CGT  ATT  GAA  GCT  ATC  CCA  CAA  ATT  GAT  AAG  TAC    576
Val  Cys  Phe  Lys  Lys  Arg  Ile  Glu  Ala  Ile  Pro  Gln  Ile  Asp  Lys  Tyr
               180                       185                       190

TTG  AAA  TCC  AGC  AAG  TAT  ATA  GCA  TGG  CCT  TTG  CAG  GGC  TGG  CAA  GCC    624
Leu  Lys  Ser  Ser  Lys  Tyr  Ile  Ala  Trp  Pro  Leu  Gln  Gly  Trp  Gln  Ala
          195                       200                       205

ACG  TTT  GGT  GGT  GGC  GAC  CAT  CCT  CCA  AAA  TCG  GAT  CTG  ATC  GAA  GGT    672
Thr  Phe  Gly  Gly  Gly  Asp  His  Pro  Pro  Lys  Ser  Asp  Leu  Ile  Glu  Gly
     210                       215                       220

CGT  GGG  ATC  CCC  CCG  GGC  TGC  AGG  AAT  TCC  ACG  AAG  GTT  GCC  GAA  GCG    720
Arg  Gly  Ile  Pro  Pro  Gly  Cys  Arg  Asn  Ser  Thr  Lys  Val  Ala  Glu  Ala
225                      230                       235                       240

GAG  AAG  CAG  AAG  GCA  GCT  GAA  GCC  ACG  AAG  GTT  GCC  GAA  GCG  GAG  AAG    768
Glu  Lys  Gln  Lys  Ala  Ala  Glu  Ala  Thr  Lys  Val  Ala  Glu  Ala  Glu  Lys
                    245                       250                       255

CAG  AGG  GCA  GCT  GAA  GCC  ACG  AAG  GTT  GCC  GAA  GCG  GAG  AAG  CAG  AAG    816
Gln  Arg  Ala  Ala  Glu  Ala  Thr  Lys  Val  Ala  Glu  Ala  Glu  Lys  Gln  Lys
               260                       265                       270

GCA  GCT  GAA  GCC  ACG  AAG  GTT  GCC  GAA  GCG  GAG  AAG  CAG  AGG  GCA  GCT    864
Ala  Ala  Glu  Ala  Thr  Lys  Val  Ala  Glu  Ala  Glu  Lys  Gln  Arg  Ala  Ala
          275                       280                       285

GAA  GCC  ACG  AAG  GTT  GCC  GAA  GCG  GAG  AAG  CAA  AAG  GCA  GCT  GAG  GCC    912
Glu  Ala  Thr  Lys  Val  Ala  Glu  Ala  Glu  Lys  Gln  Lys  Ala  Ala  Glu  Ala
     290                       295                       300

ACG  AAG  GTT  GCC  GGA  GAC  GAG  AAG  CAG  AAG  GCA  GCT  GAA  GCC  ACG  AAG    960
Thr  Lys  Val  Ala  Gly  Asp  Glu  Lys  Gln  Lys  Ala  Ala  Glu  Ala  Thr  Lys
305                      310                       315                       320
```

| | | | | | | | | | | | | | | | | |
|---|---|---|---|---|---|---|---|---|---|---|---|---|---|---|---|---|
| GTT | GCC | GAA | GCG | GAG | AAG | CAG | AAG | GCA | GCT | GAA | GCC | ACG | AAG | GTT | GCC | 1008 |
| Val | Ala | Glu | Ala | Glu | Lys | Gln | Lys | Ala | Ala | Glu | Ala | Thr | Lys | Val | Ala | |
| | | | | 325 | | | | | 330 | | | | | 335 | | |
| GAA | GCG | GAG | AAG | CAG | AAG | GCA | GCT | GAA | GCC | ACG | AAG | GTT | GCC | GAA | GCG | 1056 |
| Glu | Ala | Glu | Lys | Gln | Lys | Ala | Ala | Glu | Ala | Thr | Lys | Val | Ala | Glu | Ala | |
| | | | 340 | | | | | 345 | | | | | 350 | | | |
| GAG | AAG | CAG | AAG | GCA | GCT | GAA | GCC | ACG | AAG | GTT | GCC | GAA | GCG | GAG | AAG | 1104 |
| Glu | Lys | Gln | Lys | Ala | Ala | Glu | Ala | Thr | Lys | Val | Ala | Glu | Ala | Glu | Lys | |
| | | 355 | | | | | 360 | | | | | 365 | | | | |
| CAG | AAG | GCA | GCT | GAA | GCC | ACG | AAG | GTT | GCC | GAA | GCG | GAG | AAG | CAG | AAG | 1152 |
| Gln | Lys | Ala | Ala | Glu | Ala | Thr | Lys | Val | Ala | Glu | Ala | Glu | Lys | Gln | Lys | |
| | 370 | | | | | 375 | | | | | 380 | | | | | |
| GCA | GCT | GAA | GCC | ACG | AAG | GTT | GCC | GAA | GCG | GAG | AAG | CAG | AAG | GCA | GCT | 1200 |
| Ala | Ala | Glu | Ala | Thr | Lys | Val | Ala | Glu | Ala | Glu | Lys | Gln | Lys | Ala | Ala | |
| 385 | | | | 390 | | | | | 395 | | | | | | 400 | |
| GAA | GCC | ACG | AAG | GTT | GCC | GAA | GCG | GAG | AAG | CAG | AAG | GCA | GCT | GAA | GCC | 1248 |
| Glu | Ala | Thr | Lys | Val | Ala | Glu | Ala | Glu | Lys | Gln | Lys | Ala | Ala | Glu | Ala | |
| | | | | 405 | | | | | 410 | | | | | 415 | | |
| ACG | AAG | GTT | GCC | GAA | GCG | GAG | AAG | CAG | AAG | GCA | GCT | GAA | GCC | ACG | AAG | 1296 |
| Thr | Lys | Val | Ala | Glu | Ala | Glu | Lys | Gln | Lys | Ala | Ala | Glu | Ala | Thr | Lys | |
| | | | 420 | | | | | 425 | | | | | 430 | | | |
| GTT | GCC | GAA | GCG | GAG | AAG | CAG | AAG | GCA | GCT | GAA | GCC | ACG | AAG | GTT | GCC | 1344 |
| Val | Ala | Glu | Ala | Glu | Lys | Gln | Lys | Ala | Ala | Glu | Ala | Thr | Lys | Val | Ala | |
| | | 435 | | | | | 440 | | | | | 445 | | | | |
| GAA | GCG | GAG | AAG | CAG | AAG | GTA | GGT | GAG | GCT | GAT | CAA | GCT | TAT | CGA | TAC | 1392 |
| Glu | Ala | Glu | Lys | Gln | Lys | Val | Gly | Glu | Ala | Asp | Gln | Ala | Tyr | Arg | Tyr | |
| | 450 | | | | | 455 | | | | 460 | | | | | | |
| CGT | CGG | GAA | TTC | ATC | GTG | ACT | GAC | TGA | | | | | | | | 1419 |
| Arg | Arg | Glu | Phe | Ile | Val | Thr | Asp | | | | | | | | | |
| 465 | | | | | 470 | | | | | | | | | | | |

( 2 ) INFORMATION FOR SEQ ID NO:10:

( i ) SEQUENCE CHARACTERISTICS:
        ( A ) LENGTH: 472 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met | Ser | Pro | Ile | Leu | Gly | Tyr | Trp | Lys | Ile | Lys | Gly | Leu | Val | Gln | Pro |
| 1 | | | | 5 | | | | | 10 | | | | | 15 | |
| Thr | Arg | Leu | Leu | Leu | Glu | Tyr | Leu | Glu | Glu | Lys | Tyr | Glu | Glu | His | Leu |
| | | | 20 | | | | | 25 | | | | | 30 | | |
| Tyr | Glu | Arg | Asp | Glu | Gly | Asp | Lys | Trp | Arg | Asn | Lys | Lys | Phe | Glu | Leu |
| | | 35 | | | | | 40 | | | | | 45 | | | |
| Gly | Leu | Glu | Phe | Pro | Asn | Leu | Pro | Tyr | Tyr | Ile | Asp | Gly | Asp | Val | Lys |
| | 50 | | | | | 55 | | | | | 60 | | | | |
| Leu | Thr | Gln | Ser | Met | Ala | Ile | Ile | Arg | Tyr | Ile | Ala | Asp | Lys | His | Asn |
| 65 | | | | | 70 | | | | | 75 | | | | | 80 |
| Met | Leu | Gly | Gly | Cys | Pro | Lys | Glu | Arg | Ala | Glu | Ile | Ser | Met | Leu | Glu |
| | | | | 85 | | | | | 90 | | | | | 95 | |
| Gly | Ala | Val | Leu | Asp | Ile | Arg | Tyr | Gly | Val | Ser | Arg | Ile | Ala | Tyr | Ser |
| | | | 100 | | | | | 105 | | | | | 110 | | |
| Lys | Asp | Phe | Glu | Thr | Leu | Lys | Val | Asp | Phe | Leu | Ser | Lys | Leu | Pro | Glu |
| | | 115 | | | | | 120 | | | | | 125 | | | |
| Met | Leu | Lys | Met | Phe | Glu | Asp | Arg | Leu | Cys | His | Lys | Thr | Tyr | Leu | Asn |
| | 130 | | | | | 135 | | | | | 140 | | | | |
| Gly | Asp | His | Val | Thr | His | Pro | Asp | Phe | Met | Leu | Tyr | Asp | Ala | Leu | Asp |

-continued

```
145                           150                           155                           160
Val  Val  Leu  Tyr  Met  Asp  Pro  Met  Cys  Leu  Asp  Ala  Phe  Pro  Lys  Leu
                    165                      170                      175
Val  Cys  Phe  Lys  Lys  Arg  Ile  Glu  Ala  Ile  Pro  Gln  Ile  Asp  Lys  Tyr
               180                      185                      190
Leu  Lys  Ser  Ser  Lys  Tyr  Ile  Ala  Trp  Pro  Leu  Gln  Gly  Trp  Gln  Ala
               195                      200                      205
Thr  Phe  Gly  Gly  Gly  Asp  His  Pro  Pro  Lys  Ser  Asp  Leu  Ile  Glu  Gly
          210                      215                      220
Arg  Gly  Ile  Pro  Pro  Gly  Cys  Arg  Asn  Ser  Thr  Lys  Val  Ala  Glu  Ala
225                           230                      235                      240
Glu  Lys  Gln  Lys  Ala  Ala  Glu  Ala  Thr  Lys  Val  Ala  Glu  Ala  Glu  Lys
                    245                      250                      255
Gln  Arg  Ala  Ala  Glu  Ala  Thr  Lys  Val  Ala  Glu  Ala  Glu  Lys  Gln  Lys
                    260                      265                      270
Ala  Ala  Glu  Ala  Thr  Lys  Val  Ala  Glu  Ala  Glu  Lys  Gln  Arg  Ala  Ala
               275                      280                      285
Glu  Ala  Thr  Lys  Val  Ala  Glu  Ala  Glu  Lys  Gln  Lys  Ala  Ala  Glu  Ala
          290                      295                      300
Thr  Lys  Val  Ala  Gly  Asp  Glu  Lys  Gln  Lys  Ala  Ala  Glu  Ala  Thr  Lys
305                           310                      315                      320
Val  Ala  Glu  Ala  Glu  Lys  Gln  Lys  Ala  Ala  Glu  Ala  Thr  Lys  Val  Ala
                    325                      330                      335
Glu  Ala  Glu  Lys  Gln  Lys  Ala  Ala  Glu  Ala  Thr  Lys  Val  Ala  Glu  Ala
               340                      345                      350
Glu  Lys  Gln  Lys  Ala  Ala  Glu  Ala  Thr  Lys  Val  Ala  Glu  Ala  Glu  Lys
          355                      360                      365
Gln  Lys  Ala  Ala  Glu  Ala  Thr  Lys  Val  Ala  Glu  Ala  Glu  Lys  Gln  Lys
          370                      375                      380
Ala  Ala  Glu  Ala  Thr  Lys  Val  Ala  Glu  Ala  Glu  Lys  Gln  Lys  Ala  Ala
385                      390                      395                           400
Glu  Ala  Thr  Lys  Val  Ala  Glu  Ala  Glu  Lys  Gln  Lys  Ala  Ala  Glu  Ala
                    405                      410                      415
Thr  Lys  Val  Ala  Glu  Ala  Glu  Lys  Gln  Lys  Ala  Ala  Glu  Ala  Thr  Lys
               420                      425                      430
Val  Ala  Glu  Ala  Glu  Lys  Gln  Lys  Ala  Ala  Glu  Ala  Thr  Lys  Val  Ala
          435                      440                      445
Glu  Ala  Glu  Lys  Gln  Lys  Val  Gly  Glu  Ala  Asp  Gln  Ala  Tyr  Arg  Tyr
          450                      455                      460
Arg  Arg  Glu  Phe  Ile  Val  Thr  Asp
465                 470
```

POLYPEPTIDES FOR DIAGNOSING INFECTION WITH *TRYPANOSOMA CRUZI*

BACKGROUND OF THE INVENTION

The present invention relates to polypeptides that are useful for diagnosing American trypanosomiasis, or Chagas disease, a disease caused by the infectious agent *Trypanosoma cruzi*. More particularly, the invention relates to recombinant *T. cruzi* polypeptides, synthesized using genetic engineering techniques, and to constructs and processes for producing the recombinant polypeptides, and to an assay for detecting *T. cruzi* infection which employs the polypeptides.

American trypanosomiasis, or Chagas disease, is an illness caused by the protozoan parasite, *T. cruzi* (1,2). This organism is transmitted by insects called reduviid bugs (3), by blood transfusion (4), and also from mother to fetus (5). Several years after acquiring *T. cruzi* infection, patients may develop the cardiac and gastrointestinal symptoms that are associated with chronic infection, which is life-long, but the majority of infected persons never develop clinical manifestations of Chagas disease and are unaware of being infected. The two drugs available for treating *T. cruzi* infections have low efficacy and often cause serious side effects. In practice, therefore, they have virtually no impact on the control of Chagas disease.

Chagas disease is a major cause of morbidity and death in Latin America, where an estimated 16–18 million people are chronically infected with *T. cruzi* (6). In recent years tens of thousands of *T. cruzi*-infected people have emigrated to the United States, especially from Central America, where the prevalence of *T. cruzi* infection is high, thus creating the risk of transfusion-associated transmission of the parasite here (7–9). Several such cases have been described (10–12).

Since clinical criteria cannot be depended upon for recognizing *T. cruzi* infection, blood tests are of paramount importance, both in patient care settings and in blood banks. Chronically infected persons uniformly have anti-*T. cruzi* antibodies. The diagnosis of *T. cruzi* infection is almost always made by detecting these antibodies in patients' blood, since parasitological approaches are laborious and lack sensitivity and, as noted, clinical evaluations lack specificity.

Immunological tests currently used to diagnose *T. cruzi* infection, such as complement fixation and indirect immunofluorescence tests, and enzyme-linked immunosorbent assays (ELISA), often produce inconsistent results and false-positive reactions (13). The occurrence of false-positive reactions can be a problem with specimens from patients with leishmaniasis, schistosomiasis, and other parasitic and infectious diseases, with samples from patients with autoimmune disorders and other illnesses, and with specimens from normal persons.

In large measure these problems with sensitivity and specificity occur because the assays are based on antigens extracted from parasites grown in the laboratory. The complexity and variability of mixtures of native antigens derived from cultured parasites, which persist even after fractionation and purification procedures are used, have been a major barrier to standardization of immunoassays. Because of the limitations of these immunoassays, experts generally agree that blood samples should be positive in three different assays, performed in parallel, before being accepted as positive.

An additional problem related to assays based on material derived from cultured parasites is that producing the antigens creates a serious biohazard for technical personnel, and laboratory-acquired cases of Chagas disease occur with disquieting frequency, both in the United States and abroad (14,15). Furthermore, some of the immunoassays currently available require sophisticated laboratory equipment and levels of technical expertise not generally available in the countries in which *T. cruzi* infection is endemic.

In response to the need for improved assays for detecting *T. cruzi* infection, considerable work has been invested in the development of new immunoassays. These efforts have accelerated in recent years as new technologies have become available that have the potential for serving as the basis of improved assays. Recombinant DNA technology has led to the molecular cloning of several antigenic *T. cruzi* proteins. Cloned segments of *T. cruzi* genes have been used to produce in bacteria portions of antigenic proteins (16–22). In research settings several of these, singly and in combination, have been used as target antigens in immunoassays. These assays have not been tested in field or blood bank trials, and none is available commercially.

U.S. Pat. No. 4,870,006 discloses the use of a recombinant protein in an assay for diagnosing *T. cruzi* infection. A 70-kilodalton heat shock protein constitutes the target antigen in this assay. No information regarding the sensitivity and specificity of the assay is provided in the patent.

In this context, therefore, a need exists for a highly sensitive and specific system for detecting *T. cruzi* infection that is safe, easy, and inexpensive to manufacture and perform.

SUMMARY OF THE INVENTION

It is therefore an object of the present invention to provide a highly sensitive and specific assay for diagnosing infection with *T. cruzi*.

It is a further object of the present invention to provide an assay for diagnosing *T. cruzi* infection that is safe, inexpensive to manufacture and easy to use.

In achieving these and other objects, there has been provided, according to one aspect of the present invention, a polypeptide having a sequence that corresponds to the amino acid sequence of at least one of the C-terminal and N-terminal nonrepetitive regions of the TCR27 protein. The inventive polypeptide additionally may comprise an amino acid sequence of one or more repeats from the central region of the TCR27 protein. In a preferred embodiment, the polypeptide corresponds to the N-terminal nonrepetitive region of the TCR27 protein and at least one repeat from the central region of the TCR27 protein, and does not correspond to the C-terminal nonrepetitive region. The polypeptides may further comprise a linker sequence at either the N-terminus or the C-terminus to facilitate attachment or conjugation to a carrier molecule in a liquid or solid support system. Isolated polynucleotides that encode the inventive polypeptides according to the present invention are also claimed, as are cells transformed with a recombinant plasmid that expresses a polypeptide according to the invention.

The present invention also provides a method for detecting the presence of antibodies to *T. cruzi* in an individual, comprising the steps of contacting a putative anti-*T. cruzi* antibody-containing sample from an individual with a polypeptide according to the invention that is attached or conjugated to a carrier molecule or attached or conjugated to a solid phase; allowing anti-*T. cruzi* antibodies in said sample to bind to said polypeptide; washing away unbound anti-*T. cruzi* antibodies; and adding a compound that enables detection of the anti-*T. cruzi* antibodies which are specifically bound to the polypeptide. The compound that enables detection of the anti-*T. cruzi* antibodies may be selected from the group consisting of a colorometric agent, a fluorescent agent, a chemiluminescent agent and a radionuclide.

Also provided in accordance with the present invention is a kit for diagnosing the presence of anti-*T. cruzi* antibodies in a sample, comprising a container in which a polypeptide having a sequence that corresponds to the amino acid sequence of at least one of the C-terminal and N-terminal nonrepetitive regions of the TCR27 protein is attached or conjugated to a carrier molecule or attached or conjugated to a solid phase; and directions for carrying out the method according to the invention. The kit additionally may comprise a container of a compound that binds to anti-*T. cruzi* antibodies and that renders said antibodies detectable.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A through 2E show the nucleotide and deduced amino acid sequences (SEQ ID NOS 1–10) of polypeptides according to the present invention.

FIGS. 3A through 3F are bar graphs of results obtained when recombinant TCR27 polypeptides are used as target antigens in ELISAs to test blood samples (serum or plasma) for anti-*T. cruzi* antibodies.

DETAILED DESCRIPTION OF PREFERRED EMBODIMENTS

Figure 1:
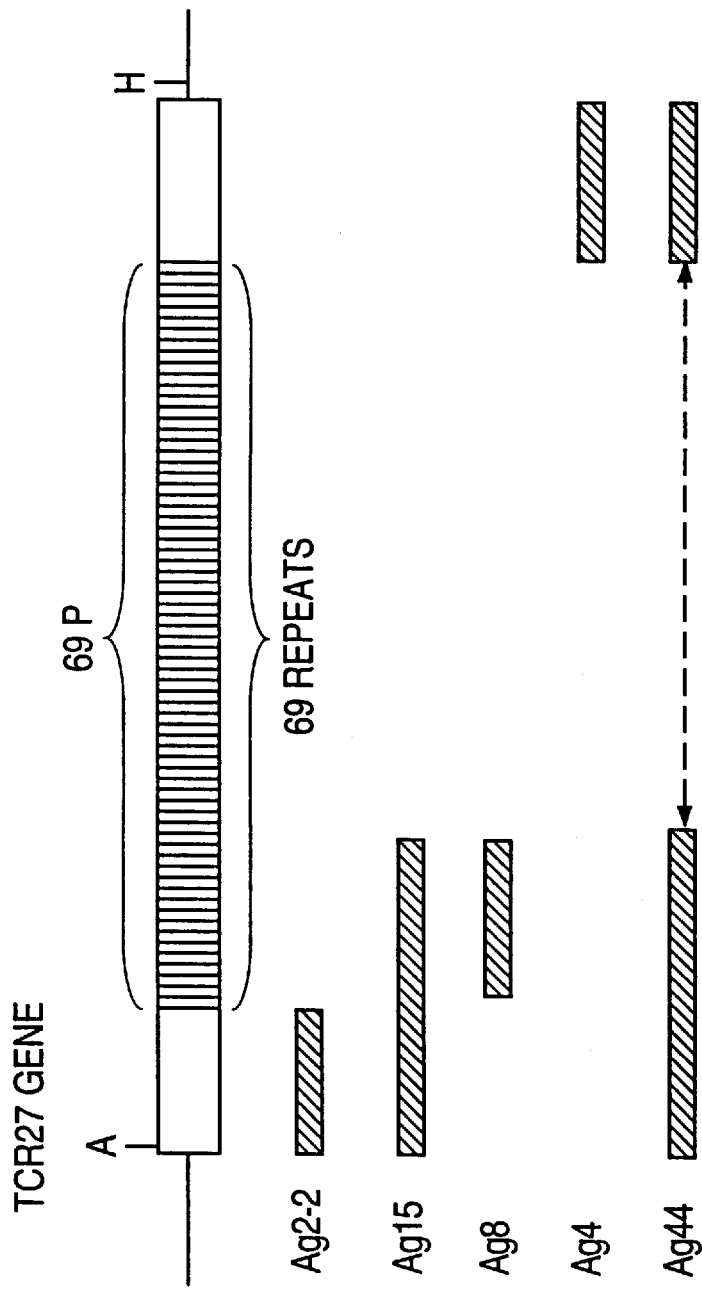
FIG. 1 is a schematic diagram of the *T. cruzi* TCR27 gene and the segments of the gene that encode polypeptides according to the present invention.

It has been discovered that a *T. cruzi* gene designated "TCR27" (23) encodes an immunodominant protein containing unique, nonrepetitive regions at both the C-terminus and N-terminus, in addition to a central region comprised of repeats of a 14-amino acid sequence. It has been further discovered that there are two copies of the TCR27 gene that essentially differ only in the number of repeats that comprise the central region. It also has been discovered that the nonrepetitive terminal regions of the TCR27 protein contain epitopes to which individuals infected with *T. cruzi* typically have antibodies. The existence of these epitopes within the nonrepetitive regions was not suggested previously.

More particularly, the native protein encoded by the TCR27 gene consists of an N-terminal 95-amino acid sequence and a C-terminal 68-amino acid sequence. A central region of repeats encodes 69 repeats of a highly-conserved, 14-amino acid sequence. In accordance with the present invention, a polypeptide that corresponds to at least one of the C-terminal or N-terminal nonrepetitive regions can form the basis for a sensitive assay to diagnose *T. cruzi* infection.

In one preferred embodiment, such a polypeptide corresponds to at least one of the C-terminal or N-terminal nonrepetitive regions in combination with a region of one or more repeats from the central region of the TCR27 protein. In a particularly preferred embodiment, a polypeptide for use in an assay according to the present invention contains the N-terminal nonrepetitive region in combination with one or more repeats from the central region of the TCR27 protein, but does not contain a region corresponding to the C-terminal nonrepetitive region. Polypeptides according to the present invention that include repeat regions in addition to one of the nonrepetitive regions will contain at least one, and preferably at least two, copies of the 14-amino acid repeat.

In addition to the nonrepetitive and repeat regions per se, a wide variety of polypeptides which contain the epitopes embodied in these regions can be used in accordance with the present invention. Based on the nucleotide sequences in FIGS. 2A through 2E (SEQ ID NOS 1, 3, 5, 7 and 9), polypeptide molecules also can be produced (1) that include sequence variations, relative to the naturally-occurring sequences, (2) that have one or more amino acids truncated from the naturally-occurring sequences and variations thereof, or (3) that contain the naturally-occurring sequences and variations thereof as part of a longer sequence.

In this description, polypeptide molecules in categories (1), (2) and (3) are said to "correspond" to the amino acid sequences of the nonrepetitive or repeat regions of the TCR27 protein. Such polypeptides also are referred to as "variants." The category of variants within the present invention includes, for example, fragments and muteins of the nonrepetitive and repeat regions, as well as larger molecules that consist essentially of one or both of the nonrepetitive sequences, alone or in combination with one or more repeats from the central region.

In this regard, a molecule that "consists essentially of" one or both of the nonrepetitive sequences, alone or in combination with one or more repeats from the central region, is one that reacts immunologically with samples from persons infected with *T. cruzi*, but that does not react with samples from patients with leishmaniasis, schistosomiasis, and other parasitic and infectious diseases, with samples from patients with autoimmune disorders and other illnesses, and with specimens from normal persons.

A "mutein" is a polypeptide that is homologous to the nonrepetitive or repeat region to which it corresponds, and that retains the basic functional attribute—the ability to react selectively with samples from persons infected with *T. cruzi*—of the corresponding region. For purposes of this description, "homology" between two sequences connotes a likeness short of identity indicative of a derivation of the first sequence from the second. In particular, a polypeptide is "homologous" to the corresponding nonrepetitive or repeat region if a comparison of amino-acid sequences between the polypeptide and the corresponding region reveals an identity of greater than 70%. Such a sequence comparison can be performed via known algorithms, such as the one described by Lipman and Pearson (24), which are readily implemented by computer. Polypeptides derived from other strains and clones of *T. cruzi* that are homologous to the sequences shown in FIGS. 2A through 2E constitute naturally-occurring muteins and are within the scope of the present invention.

A fragment of a nonrepetitive or repeat region is a molecule in which one or more amino acids are truncated from that nonrepetitive or repeat region. Muteins and fragments can be produced, in accordance with the present invention, by known de novo synthesis techniques.

Also exemplary of variants within the present invention are molecules that are longer than a nonrepetitive or a repeat region but that contain the region or a mutein thereof within the longer sequence. For example, a variant may include a fusion partner in addition to the nonrepetitive or repeat region. Such a fusion partner may allow easier purification of recombinantly-produced polypeptides. For example, use of a glutathione-S-transferase (26 kilodaltons, GST) fusion partner allows purification of recombinant polypeptides on glutathione agarose beads.

The portion of the sequence of such molecule other than that portion of the sequence corresponding to the region may or may not be homologous to the sequence of the TCR27 protein. If it is homologous with the TCR27 protein, it is not coincident with the sequence of the TCR27 protein.

It will be appreciated that polypeptides shorter than the corresponding nonrepetitive region but that retain the ability to react selectively with samples from persons infected with T. cruzi are suitable for use in the present invention. Thus, variants may be of the same length, longer than or shorter than the nonrepetitive or repeat regions, and also include sequences in which there are amino acid substitutions of the parent sequence. These variants must retain the ability to react selectively with samples from persons infected with T. cruzi.

Whether a polypeptide based on one of the sequences shown in FIGS. 2A through 2E (SEQ ID NOS 1–10) retains the ability to react selectively with samples from persons infected with T. cruzi can be determined routinely in accordance with the protocols set forth herein, that is, by reacting it with serologically well-characterized specimens from patients known to be infected with T. cruzi, and with similarly serologically well-characterized specimens from patients known to be affected with those conditions that typically cause false positive reactions in assays for antibodies to T. cruzi, such as leishmaniasis, schistosomiasis, and other parasitic and infectious diseases, with samples from patients with autoimmune disorders and other illnesses, and with specimens from normal persons.

A schematic diagram of the TCR27 gene is shown in FIG. 1. The horizontal rectangle depicts the protein encoding region of the TCR27 gene, which contains a central segment consisting of approximately 69 highly conserved repeats, each 42 nucleotides in length, flanked on both sides by dissimilar, nonrepetitive sequences. Restriction sites are indicated by A (AvaII), P (PvuII), and H (HincIII). The positions of the segments of the TCR27 gene that encode polypeptides which are representative of the present invention are indicated by the solid horizontal bars. Thus, polypeptide Ag2-2 is encoded by the nonrepetitive, upstream DNA segment of the TCR27 gene, polypeptide Ag15 by that nonrepetitive segment plus 16 of the 42-nucleotide repeat units, polypeptide Ag8 by a segment consisting of 15 of the 42-nucleotide repeat units, and polypeptide Ag4 by the nonrepetitive, downstream segment of the TCR27 gene. Also, the coding region for polypeptide Ag44 consists of the nonrepetitive, upstream coding region of the TCR27 gene, followed by a segment containing 16 repeats, followed by the nonrepetitive, downstream coding region of the TCR27 gene. The dashed double arrow indicates that the two depicted segments of Ag44 are combined in one continuous coding sequence.

FIG. 2A through FIG. 2E show the nucleotide and deduced amino acid sequences (SEQ ID NOS 1–10) for Ag15, Ag2-2, Ag4, Ag44 and Ag8, respectively. The DNA letter codes are: A, adenine; C, cytosine, G, guanine, and T, thymine. The amino acid codes are: A, alanine; C, cysteine; D, aspartic acid; E, glutamic acid; F, phenylalanine; G, glycine; H. histidine; I, isoleucine; K, lysine; L, leucine; M, methionine; N, asparagine; P, proline; Q, glutamine; R, arginine; S, serine; T, threonine; V, valine; W, tryptophan; Y, tyrosine. Stop codons are indicated by a single asterisk.

The five TCR27 gene segments that encode recombinant polypeptides according to the invention are inserted into plasmid pGEX (25). The gene encoding GST is positioned upstream from the SmaI site into which the TCR27 segments are inserted, and thus the recombinant polypeptides encoded by these plasmids have GST attached to their N-termini. The presence of GST allows purification of the recombinant polypeptides on glutathione agarose beads, as described below, but it will be readily apparent to those of ordinary skill in the art that the GST fusion partner can be cleaved from polypeptides to be used in an assay according to the invention.

FIG. 2A shows DNA and deduced amino acid sequences (SEQ ID NOS 1 and 2) of Ag15, which is a GST-TCR27 polypeptide-pGEX-2T polylinker fusion protein. GST is encoded by nucleotides 1 through 681, which are derived from pGEX-2T. The segment of the T. cruzi TCR27 protein that constitutes part of Ag15 is encoded by nucleotides 682 through 1671. The seven-amino acid sequence that constitutes the C-terminus of Ag15 is encoded by nucleotides 1672 through 1695, which is the pGEX-2T polylinker remnant that lies downstream from the SmaI site.

FIG. 2B shows DNA and deduced amino acid sequences (SEQ ID NOS 3 and 4) of Ag2-2, which is a GST-TCR27 polypeptide-pGEX-2T polylinker fusion protein. GST is encoded by nucleotides 1 through 681, which are derived from pGEX-2T. The segment of the T. cruzi TCR27 protein that constitutes part of Ag2-2 is encoded by nucleotides 682 through 1041. The seven-amino acid sequence that constitutes the C-terminus of Ag2-2 is encoded by nucleotides 1042 through 1065 which is the pGEX-2T polylinker remnant that lies downstream from the SmaI site.

FIG. 2C shows DNA and deduced amino acid sequences (SEQ ID NOS 5 and 6) of Ag4, which is a GST-TCR27 polypeptide fusion protein. GST is encoded by nucleotides 1 through 663, which are derived from pGEX-1. The segment of the T. cruzi TCR27 protein that constitutes part of Ag4 is encoded by nucleotides 664 through 924.

FIG. 2D shows DNA and deduced amino acid sequences (SEQ ID NOS 7 and 8) of Ag44, which is a GST-TCR27 polypeptide fusion protein. GST is encoded by nucleotides 1 through 681, which are derived from pGEX-2T. The segment of the T. cruzi TCR27 protein that constitutes part of Ag44 is encoded by nucleotides 682 through 1932.

FIG. 2E shows DNA and deduced amino acid sequences (SEQ ID NOS 5 and 10) of Ag8, which is a fusion protein consisting of the following polypeptides: (1) GST is encoded by nucleotides 1 through 678, which are derived from pGEX-3X; (2) a six-amino acid sequence is encoded by nucleotides 679 through 696, which are derived from the region of the polylinker region of pBluescript (26) that lies between the BamHI and EcoRI sites; (3) the segment of the T. cruzi TCR27 protein that constitutes part of Ag8 is encoded by nucleotides 697 through 1374; (4) a seven-amino acid sequence is encoded by nucleotides 1375 through 1395, which are derived from the region of the polylinker region of pBluescript that lies between the EcoRV and HincII sites ; and (5) a seven-amino acid sequence that constitutes the C-terminus of Ag8 is encoded by nucleotides 1396 through 1419 which is the pGEX-3X polylinker remnant that lies downstream from the HincII site.

The presence of GST in these five fusion polypeptides allows purification of the recombinant polypeptides on glutathione agarose beads, as described below, but it will be readily apparent to those of ordinary skill in the art that the GST fusion partner can be cleaved from polypeptides to be used in an assay according to the invention.

Polypeptides useful in an assay according to the invention can be synthetic peptides made by chemical synthesis techniques, but preferably are produced by recombinant techniques. DNA encoding the polypeptides preferably is obtained by cloning and recombination of DNA segments of the TCR27 gene. These DNA segments are utilized to produce recombinant polypeptides in bacteria. The N-termini or the C-termini of these polypeptides can be modified, respectively, to include a linker sequence that facilitates attachment or conjugation of the portions of the polypeptides that constitute the reactive epitopes to carrier molecules in solution or to solid support systems. In addition, the DNA sequences that encode the recombinant polypeptides may be modified such that the amino acid sequences described herein are not altered, or they may be altered such that the polypeptides are shortened or lengthened, or have amino acid substitutions that are preferably conservative.

The present invention further relates to methods for diagnosing *T. cruzi* infection by detecting antibodies that bind specifically to epitopes contained in the inventive polypeptides. The method consists of bringing into contact a sample of whole blood, or an antibody-containing component of blood, with a polypeptide, according to the invention, that is attached or conjugated to a carrier molecule or solid phase. After a period of contact between the sample and the polypeptide, during which antibodies in the sample are bound to the polypeptide, unbound antibodies are washed away. The bound antibodies are then visualized or otherwise detected by adding a compound or compounds that detect the antibodies which are specifically bound to the polypeptides. Exemplary of compounds that enable detection of the anti-*T. cruzi* antibodies are colorometric agents, fluorescent agents, chemiluminescent agents and radionuclides.

A significant feature of the present invention is that it enables the use of a well-defined *T. cruzi* antigen, to which a large number of infected individuals produce antibodies, in a method of diagnosing *T. cruzi* infection. In accordance with the present invention, preparations formulated from polypeptides which are produced recombinantly or by chemical synthesis, respectively, are "substantially pure." That is, they do not contain other proteins or polypeptides of *T. cruzi* origin, in contrast to antigenic preparations derived from cultured parasites. Such crude preparations are complex and variable in constituency, and typically contain a variety of *T. cruzi* antigens even after fractionation and purification procedures are used. Some of these other antigens are cross-reactive with other antibodies produced in response to other parasitic and infectious diseases, and to some noninfectious diseases as well, giving rise to false positives. This has been a major barrier to standardization of immunoassays for diagnosis of *T. cruzi*.

A high percentage of blood specimens from *T. cruzi*-infected persons from six different Latin American countries had easily demonstrable specific antibodies to polypeptides according to the invention, whereas specimens from normal persons did not. Equally important, specimens from patients with diseases that are often associated with false-positive reactions, such as leishmaniasis, schistosomiasis, and other parasitic and infectious diseases, as well as autoimmune disorders, did not produce false positives in assays with polypeptides according to the present invention. Thus, the present polypeptides are useful for diagnosing infection with *T. cruzi*.

Results of assays with various polypeptides are shown in FIGS. 3A through 3F. Two panels of specimens were used. The first panel consisted of twelve serologically well-characterized specimens from *T. cruzi*-infected patients from six Latin American countries, and twelve control specimens from healthy persons, half from Latin America and half from the United States. The second panel of specimens consisted of twelve serologically well-characterized specimens from *T. cruzi*-infected patients from five Latin American countries, and 44 control specimens from patients with the following conditions (# of patients):

visceral leishmaniasis (8)
cutaneous leishmaniasis (8)
autoimmune disease (6)
schistosomiasis (4)
toxoplasmosis (2)
pneumocystosis (2)
syphilis (1)

and healthy persons (13).

The *T. cruzi*-infected patients in the two panels were not selected because of high or low antibody titers, as determined in conventional immunoassays, and the two groups of twelve *T. cruzi*-infected patients did not overlap.

FIG. 3A presents results obtained when Ag15 was reacted with specimens in Panel 2 in an ELISA. The vertical bars indicate mean absorbance values for the *T. cruzi*-infected and uninfected groups. Standard deviations are indicated by the lines projecting from the bars. The ratio of the mean absorbance value of the *T. cruzi*-infected patients to that of the controls was 4:1, suggesting that Ag15 can serve as the basis for sensitive and specific assays for detecting *T. cruzi* infection.

Results obtained when Ag2-2 was reacted with specimens in Panel 1 in an ELISA are shown in FIG. 3B. The ratio of the mean absorbance value of the *T. cruzi*-infected patients to that of the controls was 1.5:1. While this was considerably less than the ratio of absorbance values obtained with Ag15, the results do indicate clearly that many *T. cruzi*-infected patients have antibodies that bind specifically to epitopes present on the nonrepetitive, upstream portion of the TCR27 protein and that Ag2-2 can be used in an assay for detecting *T. cruzi* infection.

FIG. 3C shows results obtained when Ag4 was reacted with specimens in Panel 1 in an ELISA. The ratio of the mean absorbance value of the *T. cruzi*-infected patients to that of the controls was 1.7:1. This ratio of absorbance values again was considerably less than the ratio obtained with Ag15, but as was the case with Ag2-2 the results indicate clearly that many *T. cruzi*-infected patients have antibodies that bind specifically to epitopes present on the nonrepetitive, downstream portion of the TCR27 protein and that an assay for detecting *T. cruzi* infection can be based on Ag4.

Results obtained when Ag44 was reacted with specimens in Panel 2 in an ELISA are presented in FIG. 3D. The ratio of the mean absorbance value of the *T. cruzi*-infected patients to that of the uninfected persons was 2:1, suggesting that Ag44 can serve as the basis for sensitive and specific assays for detecting *T. cruzi* infection.

FIG. 3E displays results obtained when Ag8 was reacted with specimens in Panel 2 in an ELISA. The ratio of the mean absorbance value of the *T. cruzi*-infected patients to that of the controls was 1.5:1. This is less than the ratios obtained with Ag15 and Ag44, thus suggesting that assays based on the latter antigens will be more discriminative than assays based on Ag8.

Results obtained when GST alone was reacted with specimens in Panel 2 in an ELISA are displayed in FIG. 3F. The ratio of the mean absorbance value of the *T. cruzi*-infected patients to that of the controls is 1:1, indicating unambiguously that the ability of the assays based on the recombinant TCR27 proteins to discriminate between specimens from *T. cruzi*-infected patients and those of controls is based on antibody binding to the *T. cruzi* portions of the fusion proteins, rather than on reactivity with GST.

The present invention can be understood further with reference the following, non-limiting examples.

EXAMPLE 1

Propagation and Isolation of Parasites

Epimastigotes of the Sylvio X-10/4 clone of *T. cruzi* (27) were maintained in logarithmic growth phase at 26° C. in supplemented liver digest neutralized medium and harvested as described earlier (28). Mixtures of epimastigotes and culture-derived metacyclic trypomastigotes (CMT)(~1:1) were produced in supplemented Grace's insect medium, and purified CMT (>90%) were obtained by passing the mixture through a DE52 column.

EXAMPLE 2

Construction of CDNA Expression Library

RNA was isolated from purified Sylvio X-10/4 CMT as described (29) and cDNAs were synthesized from total RNA, without prior isolation of poly(A)$^+$ RNA, with Moloney murine leukemia virus reverse transcriptase in the BRL Synthesis System (Bethesda Research Laboratories, Gaithersburg, Md.). After treatment of the cDNAs with EcoRI methylase, EcoRI linkers were attached and the cDNAs were ligated into bacteriophage ZAP (Stratagene, San Diego, Calif.). After packaging of the recombinant phage with GigaPack Gold (Stratagene), a library of $6.4\times10^6$ independent clones was obtained, and $5\times10^6$ clones were amplified in *E. coli* Y1090.

EXAMPLE 3

Immunoscreening the cDNA Library and Isolation of a TCR27 cDNA

Serum from a Bolivian patient with clinically apparent Chagas disease, whose infection with *T. cruzi* had been established parasitologically and by conventional serologic assays (30), was used for immunoscreening. The amplified cDNA library was immunoscreened as described previously (31) using horseradish peroxidase-conjugated goat anti-immunoglobulin G as secondary antibody. Approximately 30 strongly reactive phage were identified, and recombinant pBluescript plasmids were recovered from purified reactive ZAP clones by coinfecting *E. coli* XL1-Blue with the recombinant phage and R408 helper phage (26). Nucleotide sequences of cloned cDNAs were determined using the Sequenase kit (U.S. Biochemicals, Cleveland, Ohio).

One of the cDNAs isolated by this approach, designated "TCR27," is 1,660 nucleotides in length and has a 1,230 nucleotide single open reading frame as well as a poly A tail. The upstream segment of this cDNA encodes 25 highly conserved 14-amino acid repeats, and the portion of the coding region downstream from this repetitive region encodes a dissimilar and nonrepetitive 68-amino acid sequence (17).

EXAMPLE 4

Construction of the Genomic Library and Isolation of a Full-Length TCR27 Gene Genomic DNA was isolated from $6\times10^9$ Sylvio X-10/4 epimastigotes as described (32). A genomic library was constructed in bacteriophage FIX using the procedures suggested by the supplier of the vector (Stratagene). Approximately 100,000 phage plaques were screened by hybridizing radiolabeled TCR27 cDNA to phage DNA bound to nitrocellulose filters using standard procedures (33). Six recombinant phage-bearing inserts containing at least a segment of a TCR27 gene were identified, and one, which was approximately 9.5 kilobases in length, was characterized in detail after cloning into plasmid pBluescript.

DNA of the pBluescript clone bearing the 9.5 kilobase TCR27 fragment was prepared as described (33) and analyzed by digestion with various restriction endonucleases, electrophoresis in 1% agarose gels, and visualization under UV illumination. Information obtained through restriction mapping and DNA sequencing, performed using the Sequenase kit (U.S. Biochemicals) and on an automated DNA sequencer (ABI, Foster City, Calif.) was used to construct the schematic diagram of the TCR27 gene shown in FIG. 1. The salient features of the TCR27 gene include a ~2.9 kilobase central region that encodes 69 of the highly conserved 14-amino acid repeats. This central region is flanked upstream and downstream by dissimilar and nonrepetitive regions that encode 95- and 68-amino acid sequences respectively.

EXAMPLE 5

Construction of Recombinant Plasmids Containing Segments of the TCR27 Gene

Plasmid encoding Ag15.

Recombinant pBluescript DNA bearing the TCR27 gene was digested with AvaII and HincII and the resulting 3.8 kilobase fragment, after isolation by electrophoresis and filling in the AvaII end, was cloned into the SmaI site of pGEX-2T (Pharmacia Biotech, Piscataway, N.J.) (25) using standard procedures (33). After production of DNA of the latter recombinant plasmid, designated pTCR27-7, a BamHI-EcoRI fragment was isolated and was subjected to partial digestion with PvuII, which cuts in the 42-nucleotide TCR27 repeat sequence. The resulting mixture of DNA fragments containing variable numbers of repeats was then cloned into pGEX-2T which had been digested previously with SmaI and BamHI. After cloning of the resulting recombinant plasmids, the sizes of their inserts were determined by BamHI-EcoRI digestion and electrophoresis. A plasmid containing a ~850 nucleotide insert, designated pGEX-2T-Ag15, was selected for further evaluation. The presence at the upstream end of this insert of the 5' nonrepetitive segment of the TCR27 coding region and the 42-nucleotide repeats at its 3' terminus was confirmed by DNA sequencing, as was the in-frame positioning of the region that encodes the recombinant protein. When Ag15 was produced in *E. coli* as described below, a protein of the expected size was present in a Coomassie blue-stained gel, and this protein reacted with an anti-TCR27 repeat serum in a Western blot. This latter serum was produced by immunizing a rabbit with a synthetic peptide consisting of two 14-amino acid TCR27 repeats.

Plasmid encoding Ag44.

Beginning with pTCR27-7 DNA (see Ag15 above) a BamHI-EcoRI fragment was isolated and subjected to partial digestion with PvuII and fragments ~0.5–0.75 kilobases were isolated from the resulting mixture. This mixture of fragments was then treated with ligase to generate BamHI-EcoRI fragments similar to the native TCR27 coding region, but with far fewer repeats in their central regions. The resulting fragments were then cloned into pGEX-2T previously digested with BamHI and EcoRI. The sizes of the inserts in the resulting recombinant plasmids were determined by BamHI and EcoRI digestion and electrophoresis, and one containing a ~1.1 kilobase insert, designated pGEX-2T-Ag44, was selected for further evaluation. The presence at the upstream end of this insert of the 5' nonrepetitive segment of the TCR27 coding region and the 3' nonrepetitive segment at its 3' terminus, as well as the presence of an intervening region of repeats, was confirmed by DNA sequencing. In addition, the in-frame positioning of the 5' end of the coding region of the construct was confirmed by this approach. When Ag44 was produced in E. coli as described below, a protein of the expected size was present in a Coomassie blue-stained gel, and this protein reacted with the anti-TCR27 repeat serum in a Western blot.

Plasmid encoding Aq2-2.

pGEX-2T-Ag44 DNA was digested to completion with BamHI and PvuII, and fragments ~350 nucleotides in length were cloned into pGEX-2T previously digested with BamHI and SmaI. The presence in one of the resulting plasmids of the 5' nonrepetitive coding region of the TCR27 gene was confirmed by DNA sequencing, as was a lack of repeats and the in-frame positioning of the insert. As with the other recombinant antigens, an appropriately sized protein was produced in E. coli.

Plasmid encoding Ag4.

pGEX-2T-Ag44 DNA was digested to completion with PvuII and EcoRI, and fragments ~350 nucleotides in length were cloned into pGEX-1 previously digested with SmaI and EcoRI. The presence in one of the resulting plasmids of the 3' nonrepetitive coding region of the TCR27 gene was confirmed by DNA sequencing, as was a lack of repeats and the in-frame positioning of the insert. As with the other recombinant antigens, an appropriately sized protein was produced in E. coli.

Plasmid encoding Aq8.

An EcoRI-HincII fragment of the TCR27 cDNA was cloned into pbluescript SK that had been previously digested with these two endonucleases. The resulting recombinant plasmid was linearized with HincII and then digested with Bal 31 with the purpose removing the 3' nonrepetitive region while leaving a region of repeats. A fragment obtained by this approach was shown to have a segment containing ~700 nucleotides of repetitive sequence and was cloned into pbluescript. The presence of repeats at both ends of this insert was confirmed by DNA sequencing. The insert, as a BamHI-HincII fragment, was then excised from pbluescript and cloned into the BamHI-SmaI site of pGEX-3X. When Ag8 was produced in E. coli a protein of the expected size was seen in a Coomassie blue stained gel, and this protein reacted with antibodies in the anti-TCR27 repeat serum.

EXAMPLE 6

Expression in E. coli and Purification of Recombinant Polypeptides

For the production of recombinant polypeptides, E. coli DH5 ſ transformed with pGEX bearing a TCR27 coding segment, was grown overnight at 37° C. in liquid LB medium containing 100 μg/ml ampicillin. One-tenth volume of this culture was then inoculated into approximately 80 ml fresh LB/amp medium, and after incubation for 1 hour, isopropyl-β-D-thiogalactopyranoside was added to a concentration of 0.1 mM and the culture was further incubated for 3–7 hours at 37° C. The culture was then centrifuged at 3,000×g for 15 minutes at 4° C., and after aspiration of the supernatant the pellet was suspended to 2.5 ml in phosphate buffered saline (PBS) containing 1% Triton X-100 and 1.6 mM phenylmethylsulfonyl fluoride to inhibit proteolysis. The cell suspension was sonicated until it became bubbly and then centrifuged at 10,000×g for 10 minutes.

Partial purification of the recombinant polypeptides was accomplished by mixing the above supernatant with 200 μl of 50% glutathione-agarose beads (Sigma, St. Louis, Mo.) suspended in PBS and incubating at room temperature for 1 hour with gentle shaking. The beads were then washed 2 times with 0.5% Triton X-100 and 1.6 mM phenylmethylsulfonyl fluoride in PBS, followed by a single wash with PBS. To remove the recombinant protein from the beads, 200 μl of 10 mM glutathione in 50 mM Tris-HCl, pH 8 was added and incubated for 10 minutes at room temperature with gentle shaking, and the beads are pelleted in a microcentrifuge. This procedure was repeated once and the supernatants obtained were combined, after which the protein concentration was determined using a protein assay kit (Bio-Rad, Richmond, Calif.).

EXAMPLE 7

ELISA for Detecting T. cruzi Infection

To test blood samples for antibodies that bind specifically to the recombinant T. cruzi antigens, the following procedure was employed. After purification on glutathione agarose, the recombinant antigen was diluted in PBS to a concentration of 5 ug/ml (500 ng/100 μl). One hundred microliters of the diluted antigen solution was added to each well of a 96-well Immulon 1 plate (Dynatech Laboratories, Chantilly, Va.), and the plate was then incubated for 1 hour at room temperature, or overnight at 4° C., and washed 3 times with 0.05% Tween 20 in PBS. Blocking to reduce nonspecific binding of antibodies was accomplished by adding to each well 20 μl of a 1% solution of bovine serum albumin in PBS/Tween 20 and incubation for 1 hour. After aspiration of the blocking solution, 100 μl of the primary antibody solution (anticoagulated whole blood, plasma, or serum), diluted in the range of ⅟₁₆ to ⅟₂₀₄₈ in blocking solution, was added and incubated for 1 hour at room temperature or overnight at 4° C. The wells were then washed 3 times, and 100 μl of goat anti-human IgG antibody conjugated to horseradish peroxidase (Organon Teknika, Durham, N.C.), diluted ⅟₅₀₀ or ⅟₁₀₀₀ in PBS/Tween 20, 100 μl of o-phenylenediamine dihydrochloride (OPD, Sigma) solution was added to each well and incubated for 5–15 minutes. The OPD solution was prepared by dissolving a 5 mg OPD tablet in 50 ml 1% methanol in $H_2O$ and adding 50 μl 30% $H_2O_2$ immediately before use. The reaction was stopped by adding 25 l of 4M $H_2SO_4$. Absorbances were read at 490 nm in a microplate reader (Bio-Rad).

REFERENCES

1. Brener Z. Biology of Trypanosoma cruzi. Ann.Rev.Microbiol. 1973;27:347–82.
2. Kirchhoff L. V. Trypanosoma species (American trypanosomiasis, Chagas disease): Biology of trypanosomes. In: Mandell G. L., Bennett J. E., Dolin R, eds. Principles and Practice of Infectious Diseases. 4th ed. New York: John Wiley & Sons; 1994.
3. Lent H, Wygodzinsky P. Revision of the Triatominae (Hemiptera, Reduviidae), and their significance as vectors of Chagas' disease. Bull Am Museum Natural History. 1979;163:123–520.
4. Schmunis G. A. Trypanosoma cruzi, the etiologic agent of Chagas' disease: status in the blood supply in endemic and nonendemic countries. Transfusion. 1991;31:547–57.

5. Azogue E, La Fuente C, Darras C. H. Congenital Chagas' disease in Bolivia: epidemiological aspects and pathological findings. Trans R Soc Trop Med Hyg. 1985;79:176–80.
6. WHO Expert Committee. Control of Chagas Disease (WHO Technical Report Series 811). Geneva: World Health Organization; 1991.
7. Kirchhoff L. V., Gam A. A., Gilliam F. C. American trypanosomiasis (Chagas' disease) in Central American immigrants. Am J Med. 1987;82:915–20.
8. Kirchhoff L. V. Is *Trypanosoma cruzi* a new threat to our blood supply?. Ann Intern Med. 1989;111:773–5.
9. Kerndt P. R., Waskin H. A., Kirchhoff L. V., et al. Prevalence of antibody to *Trypanosoma cruzi* among blood donors in Los Angeles, Calif. Transfusion. 1991;31:814–8.
10. Geiseler P. J., Ito J. I., Tegtmeier B. R., Kerndt P. R., Krance R. Fulminant Chagas disease (CD) in bone marrow transplantation (BMT). Abstracts of the 1987 Interscience Conference on Antimicrobial Agents and Chemotherapy. 1987; 169[Abstract].
11. Grant I. H., Gold J. W. M. , Wittner M, et al. Transfusion-associated acute Chagas disease acquired in the United States. Ann Intern Med. 1989;111:849–51.
12. Nickerson P, Orr P, Schroeder M, Sekla L, Johnston J. B. Transfusion-associated *Trypanosoma cruzi* infection in a non-endemic area. Ann Intern Med. 1989;111:851–3.
13. Camargo M. E. American Trypanosomiasis (Chagas' Disease). In: Balows A, Hausler W. J. J, Lennette E. H., eds. Laboratory Diagnosis of Infectious Diseases— Principles and Practice. New York: Springer-Verlag; 1988:744–53.
14. Brener Z. Laboratory-Acquired Chagas' Disease: An Endemic Disease Among Parasitologists?. In: Morel C. M., ed. Genes and Antigens of Parasites: A Laboratory Manual. 2nd ed. Rio de Janero: Oswaldo Cruz; 1984:3–9.
15. Hofflin J. M., Sadler R. H., Araujo F. G. Laboratory-acquired Chagas' disease. Trans R Soc Trop Med Hyg. 1987;81:437–40.
16. Ibanez C. F., Affranchino J. L., Macina R. A., et al. Multiple *Trypanosomia cruzi* antigens containing tandenly repeated amino acid sequence motifs. Mol Biochem Parasitol. 1988;30:27–34.
17. Hoft D. F., Kim K. S., Otsu K, et al. *Trypaiosonia cruzi* expresses diverse repetitive protein antigens. Infect Immun. 1989;57:1959–67.
18. Cotrim P. C., Paranhos G. S., Mortara R. A., et al. Expression in *Escherichia coli* of a dominant immunogen of *Trypanosoma cruzi* recognized by human chagasic sera. J Clin Microbiol. 1990;28:519–24.
19. Moncayo A, Luquetti A. O. Multicentre double blind study for evaluation of *Trypanosoma cruzi* defined antigens as diagnostic reagents. Mem Inst Oswaldo Cruz. 1990;85:489–95.
20. Frasch A. C. C., Cazzulo J. J., Aslund L, Pettersson U. Comparison of genes encoding *Trypanosoma cruzi* antigens. Parasitol Today. 1991;7:148–51.
21. Levin M. J., da Silveira J. F., Frasch A. C. C, et al. Recombinant *Trypanosoma cruzi* antigens and Chagas' disease diagnosis: analysis of a workshop. FEMS Microbiol Immunol. 1991;4:11–9.
22. Burns Jr., Shreffler W. G., Rosman D. E., Sleath P. R., March C. J., Reed S. G. Identification and synthesis of a major conserved antigenic epitope of *Trypanosoma cruzi*. Proc Natl Acad Sci USA. 1992;89:1239–43.
23. Otsu K, Donelson J. E., Kirchhoff L. V. Interruption of a *Trypanosoma cruzi* gene encoding a protein containing 14-amino acid repeats by targeted insertion of the neomycin phosphotransferase gene. Mol Biochem Parasitol. 1993;57:317–30.
24. Lipman D. J., Pearson W. R. Rapid and sensitive protein similarity searches. Science. 1985;227:1435–41.
25. Smith D. B., Johnson K. S. Single-step purification of polypeptides expressed in *Eschericia coli* as fusions with glutathione S-transferase. Gene. 1988;67:31–40.
26. Short J. M., Fernandez J. M., Sorge J. A., Huse W. D. Lambda ZAP: a bacteriophage lambda expression vector with in vivo excision properties. Nucleic Acids Res. 1988;16:7583–600.
27. Silveira F. T., Dias M. G., Pardal P. P., de Oliveira Loboa A, de Britto Melo G. Nono caso autoctone de doenca de Chagas registrado no estado do Para, Brasil (Nota Previa). Hileia Med Belem. 1979;1:61–2.
28. Kirchhoff L. V., Hieny S, Shiver G. M., Snary D, Sher A. Cryptic epitope explains the failure of a monoclonal antibody to bind to certain isolates of *Trypanosoma cruzi*. J Immunol. 1984;133:2731–5.
29. Chirgwin J. M., Prybuyla A. E., MacDonald R. J., Rutter W. J. Isolation of biologically active ribonucleic acid from sources enriched in ribonuclease. Biochemistry. 1979;18:5294–9.
30. Kirchhoff L. V., Neva F. A. Chagas' disease in Latin American immigrants. JAMA. 1985;254:3058–60.
31. Huynh T. V., Young R. A., Davis R. W. Constructing and screening cDNA libraries in lambda gt10 and lambda gt11. In: Glover D. M., ed. DNA Cloning Techniques: A Practical Approach. Oxford: IRL Press; 1985:49–78.
32. Laurent M, Van Assel S, Steinert M. Kinetoplast DNA. A unique macromolecular structure of considerable size and mechanical resistance. Biochem Biophys Res Commun. 1971;43:278–84.
33. Sambrook J, Fritsch E. F., Maniatis T. Molecular cloning: a laboratory manual. 2nd ed. Cold Spring Harbor, N.Y.: Cold Spring Harbor Laboratory Press; 1989.

What we claim is:

1. An isolated polypeptide having the sequence of SEQ ID NO. 2.

2. An isolated non-native polypeptide including the sequence of SEQ ID NO. 2.

3. The isolated non-native polypeptide of claim 2 wherein said polypeptide is a fusion polypeptide.

4. An isolated polypeptide having the sequence of SEQ ID NO. 4.

5. An isolated non-native polypeptide including the sequence of SEQ ID NO. 4.

6. The isolated non-native polypeptide of claim 5 wherein said polypeptide is a fusion polypeptide.

* * * * *